(12) United States Patent
Mazzoleni

(10) Patent No.: US 11,666,051 B2
(45) Date of Patent: Jun. 6, 2023

(54) COMPOSITION COMPRISING NUCLEIC ACIDS OF PARASITIC, PATHOGENIC OR INFESTING BIOLOGICAL SYSTEMS FOR INHIBITING AND/OR CONTROLLING THE GROWTH OF SAID SYSTEMS AND PROCESS FOR THE PREPARATION THEREOF

(71) Applicant: NO SELF S.R.L., Naples (IT)

(72) Inventor: Stefano Mazzoleni, Naples (IT)

(73) Assignee: NO SELF S.R.L., Naples (IT)

( * ) Notice: Subject to any disclaimer, the term of this patent is extended or adjusted under 35 U.S.C. 154(b) by 525 days.

(21) Appl. No.: 16/537,436

(22) Filed: Aug. 9, 2019

(65) Prior Publication Data

US 2020/0205413 A1    Jul. 2, 2020

Related U.S. Application Data

(63) Continuation of application No. 14/418,337, filed as application No. PCT/IT2013/000193 on Jul. 10, 2013, now Pat. No. 10,420,343.

(30) Foreign Application Priority Data

Aug. 2, 2012  (IT) .......................... NA2012A000046

(51) Int. Cl.

| C12N 5/14 | (2006.01) |
|---|---|
| C12N 1/21 | (2006.01) |
| C12N 1/15 | (2006.01) |
| C12N 1/19 | (2006.01) |
| A01N 57/16 | (2006.01) |
| C12M 1/00 | (2006.01) |
| C12N 1/10 | (2006.01) |
| C12N 1/12 | (2006.01) |
| C12N 1/14 | (2006.01) |
| C12N 1/20 | (2006.01) |
| C12N 5/04 | (2006.01) |

(52) U.S. Cl.
CPC ............ *A01N 57/16* (2013.01); *C12M 29/18* (2013.01); *C12M 47/12* (2013.01); *C12N 1/10* (2013.01); *C12N 1/12* (2013.01); *C12N 1/14* (2013.01); *C12N 1/20* (2013.01); *C12N 5/04* (2013.01); *Y02A 50/30* (2018.01); *Y02A 90/40* (2018.01)

(58) Field of Classification Search
None
See application file for complete search history.

(56) References Cited

U.S. PATENT DOCUMENTS

| 10,420,343 B2 | 9/2019 | Mazzoleni |
| 2007/0036778 A1 | 2/2007 | Meinke et al. |
| 2008/0171337 A1 | 7/2008 | Miyazaki et al. |
| 2009/0269812 A1 | 10/2009 | Sawai et al. |
| 2015/0189887 A1 | 7/2015 | Mazzoleni |
| 2020/0205413 A1 | 7/2020 | Mazzoleni |
| 2022/0132866 A1 | 5/2022 | Diano et al. |

FOREIGN PATENT DOCUMENTS

| CA | 2880411 A1 | 2/2014 |
| CN | 101553572 A | 10/2009 |
| CN | 107788014 B | 1/2021 |
| EP | 1944368 A1 | 7/2008 |
| EP | 1988170 A1 | 11/2008 |
| EP | 2182065 A2 | 5/2010 |
| EP | 2802213 A2 | 11/2014 |
| EP | 3425039 A1 | 1/2019 |
| JP | 2007523609 A | 8/2007 |
| JP | 2008167722 A | 7/2008 |
| JP | 2011067160 A | 4/2011 |
| JP | 2012065603 A | 4/2012 |
| JP | 2015524436 A | 8/2015 |
| WO | 2005/049841 A1 | 6/2005 |
| WO | 2010/001841 A1 | 1/2010 |
| WO | 2011/031520 A1 | 3/2011 |
| WO | 2011/112570 A1 | 9/2011 |
| WO | 2014/020624 A2 | 2/2014 |
| WO | 2014/020624 A3 | 5/2014 |
| WO | 2019/079656 A1 | 4/2019 |
| WO | 2019/079656 A8 | 5/2019 |

(Continued)

OTHER PUBLICATIONS

Second Office Action for CN Application No. 201710993629.4 filed on Jul. 10, 2013, on behalf of NO SELF SRL, dated Apr. 28, 2021. Chinese + English Translation. 13 pages.
ABCAM "A Beginner's Guide to ChIP", (2011). 32 pages.
Alberghina, L. et al., "Cell Growth and Cell Cycle in *Saccharomyces cerevisiae*: Basic Regulatory Design and Protein-Protein Interaction Network", Biotechnology Advances, 30, pp. 52-72, (2012).
Bailey, J.E. et al., "Kinetics of Substrate Utilization, Product Formation, and Biomass Production in Cell Cultures", Biochemical Engineering Fundamentals, MacGraw-Hill International Editions, New York, 2nd Edition, p. 373, (1986), 3 pages.

(Continued)

*Primary Examiner* — Celine X Qian
(74) *Attorney, Agent, or Firm* — Steinfl + Bruno LLP

(57) ABSTRACT

The present disclosure describes a DNA fragment mixture for the prevention or for the treatment of at least one pathogenic, parasitic or infesting species of plants or of the environment, wherein the DNA mixture consists of random fragments of total DNA of at least one pathogenic, parasitic, or infesting species, and/or at least one phylogenetically similar species, against which the prevention and treatment are directed. Further, the disclosure describes a process and related system for improvement of the production/growth of microorganisms at high yield in bioreactors or photobioreactors, or of plants in different culture systems, where the nucleic acids of the organisms produced/grown by such a process are removed from the culture medium and the culture medium, deprived of these nucleic acid, is used again in the process.

14 Claims, 16 Drawing Sheets

(56) References Cited

FOREIGN PATENT DOCUMENTS

WO 2020/167128 A1 8/2020

OTHER PUBLICATIONS

Berne, C. et al., "A Bacterial Extracellular DNA Inhibits Settling of Motile Progeny Cells Within a Biofilm", Molecular Biology, 77(4), pp. 815-829, (2010).
Bonanomi, G. et al., "Identifying the Characteristics of Organic Soil Amendments that Suppress Soilborne Plant Diseases", Soil Biology & Biochemistry, 42, pp. 136-144, (2010).
Brent, K.J. et al., "Fungicide Resistance in Crop Pathogens: How can it be Managed?", Croplife International, Brussel, (2007). 60 pages.
Burnett, J.C. et al., "RNA-Based Therapeutics: Current Progress and Future Prospects", Chemistry & Biology, vol. 19, pp. 60-71, (Jan. 27, 2012).
"Cell Proliferation", Nature.com, 1 pg. (Jun. 1, 2017), www.nature.com/subjects/cell-proliferation.
Clatworthy, A.E. et al., "Targeting Virulence: A New Paradigm for Antimicrobial Therapy", Nature Chemical Biology, vol. 3, No. 9, pp. 541-548, (Sep. 2007).
Communication pursuant to Article 94(3) EPD for European Patent Office Application No. EP18184242.8 filed on behalf of No Self S.r.l. on Jul. 10, 2013, dated Oct. 29, 2020. 5 pages.
De Ley et al. "The Quantitative Measurement of DNA Hybridization from Renaturation Rates", Eur J Biochem.Jan. 1970;12(1):133-142.
Dell'anno, A. et al., "Extracellular DNA Plays a Key Role in Deep-Sea Ecosystem Functioning", Science, vol. 309, p. 2179, (Sep. 30, 2005).
Deshmukh, V.P. et al., "A Simple Method for Isolation of Genomic DNA from Fresh and Dry Leaves of Terminalia Arjuna (Roxb.) Wight and Argot", Electronic Journal of Biotechnology, vol. 10, No. 3, pp. 468-472, (Jul. 15, 2007).
Diagenode "Standard Protocols DNA Shearing for Bioruptor Pico", (Jun. 2, 2013). 5 pages.
Ding et al. "Large-scale screening of intracellular protein localization in living fission yeast cells by the use of a GFP-fusion genomic DNA library" Genes to Cells, Blackwell Science Limited. 2000. vol. 5. pp. 169-190. 23 pgs.
European Patent Office Communication pursuant to Article 94(3) EPC in relation to Application No. 13 756 711.1-1454, dated Jan. 16, 2015. 6 pages.
Examination Report No. 1 for standard patent application for Australian Application No. 2017213527 filed Aug. 10, 2017, dated Jan. 10, 2019. 3 pages.
Fan, X. et al., "Extensive Chromatin Fragmentation Improves Enrichment of Protein Binding Sites in Chromatin Immunoprecipitation Experiments", Nucleic Acids Research, vol. 36, No. 19, e125, (2008). 7 pages.
First OA for Chinese Application No. 201710993629.4, dated Jul. 28, 2020. Original and English translation. 21 pages.
Gahan, P.B., "Circulating DNA: Intracellular and Intraorgan Messenger?", Annals of the New York Academy of Sciences, (2006), 1075, 1, 21-33. Doi: 10.1196/annals.1368.003.
Gaines, T.A. et al., "Gene Amplification Confers Glyphosate Resistance in Amaranthus Palmeri", PNAS, vol. 107, No. 3, pp. 1029-1034, (Jan. 19, 2010).
Ge, X. et al., "Rapid Vacuolar Sequestration: The Horseweed Glyphosate Resistance Mechanism", Pest Management Sci., 66(4), pp. 345-348, (Apr. 2010). 7 pages.
Gruenert, D. et al., "Sequence-Specific Modulation of Genomic DNA by Small DNA Fragments", Journal of Clinical Investigation, vol. 112, No. 5, pp. 637-641, (Sep. 2003).
Hidayat, I. et al., "Enhanced Metabolism of Fluazifop Acid in a Biotype of Digitaria Sanguinalis Resistant to the Herbicide Fluazifop-P-Butyl", Pesticide Biochemistry and Physiology, 57, pp. 137-146, (1997).
International Preliminary Report on Patentability for PCT/IT2013/000193 filed Jul. 10, 2013 on behalf of No Self S.R.L, dated Feb. 3, 2015. 12 pages.
International Search Report for International Application No. PCT/IT2013/000193 filed Jul. 10, 2013 on behalf of No. Self S.R.L, dated Mar. 21, 2013. 6 pages.
Kirkpatrick, C. et al., "Cell dispersal in biofilms: an extracellular DNA masks nature's strongest glue" Molecular Microbiology 77(4). 801-804. (Jun. 2010).
Lebaron, H. et al., "Herbicide Resistance in Plants", Wiley, New York, (1982). 30 pages.
Lee, T.I. et al., "Chromatin Immunoprecipitation and Microarray-Based Analysis of Protein Location", Nat. Protoc., 1(2), pp. 729-748, (2006). 35 pages.
Levy-Booth, D. et al., "Cycling of Extracellular DNA in the Soil Environment", Soil Biology & Biochemistry, 39, pp. 2977-2991, (2007). 16 pages.
Madigan, M.T. et al., "Microbial Growth Control", Brock: Biology of Microorganisms (9th Edition), Prentice-Hall, Inc., pp. 741-742 and 749-751, (2000), 7 pages.
Mann, T. et al., "The Application of Ultrasound as a Rapid Method to Provide DNA Fragments Suitable for Detection by DNA Biosensors", Biosensors and Bioelectronics, vol. 20, pp. 945-955, (2004).
Morgan, S. et al., "The Cost of Drug Development: A Systematic Review", Health Policy, 100, pp. 4-17, (2011).
Mulcahy, H. et al., "Extracellular DNA Chelates Cations and Induces Antibiotic Resistance in Pseudomonas Aeruginosa Biofilms", vol. 4, Issue 11, e1000213, (Nov. 2008). 12 pages.
Nielsen, K. et al., "Release and Persistence of Extracellular DNA in the Environment", Environmental Biosafety Research, vol. 6, pp. 37-53, (2007).
Office Action for Japanese Application No. JP2018011630 filed on Jul. 19, 2016, dated Feb. 12, 2019. Original and English translation. 7 pages.
Patil, S. et al., "DNA-Based Therapeutics and DNA Delivery Systems: A Comprehensive Review", The AAPS Journal, 7(1), Article 9, E61-E77, (2005).
Paungfoo-Lonhienne, C. et al., "DNA is Taken Up by Root Hairs and Pollen, and Stimulates Root and Pollen Tube Growth", Plant Physiology, vol. 153, pp. 799-805, (Jun. 2010).
Peabody Museum Webpage—"What is a Phylogenetic Relationship?", 2008. peabody.yale.edu/exhibits/tree-of-life/what-phylogenetic-relationship. Yale Peabody Museum. 3 pages.
Peter Landwall, et al., "Removal of Inhibitors of Bacterial Growth by Dialysis", Journal of General Microbiology, (1977), 103, 2,345-352.
Peters, D.L. et al., "Origin, Translocation and Destination of Extracellular Occurring DNA—A New Paradigm in Genetic Behaviour", Clinica Chimica Acta, 412, pp. 806-811, (2011).
Pinchuk, G. et al., "Utilization of DNA as a Sole Source of Phosphorous, Carbon, and Energy by Shewanella spp.: Ecological and Physiological Implications for Dissimilatory Metal Reduction", Applied and Environmental Microbiology, vol. 74, No. 4, pp. 1198-1208, (Feb. 2008). 12 pages.
Powles, S. et al., "Herbicide Resistance and World Grains", CRC Press, New York, (2001). 33 pages.
Prather, T.S. et al., "Herbicide Resistance: Definition and Management Strategies", University of California, Division of Agricultures and Natural Resources, Oakland, (2000). 14 pages.
Ryan, G.F. "Resistance of Common Groundsel to Simazine and Atrazine", Weed Science, vol. 18, pp. 614-616, (1970). 4 pages.
Search Report for International Application No. IT NA20120046 filed Aug. 2, 2012 on behalf of No Self S.R.L, dated May 17, 2013. 2 pages.
Sibley andAhlquist, "The Phylogeny of theHominoid Primates, as Indicated by DNA-DNA Hybridization", J Mol Evol (1984) 20(1):2-15.
Steffan, R. et al., "Recovery of DNA from Soils and Sediments", Applied and Environmental Microbiology, vol. 54, No. 12, pp. 2908-2915, (Dec. 1988). 9 pages.
Steinberger, R. et al., "Extracellular DNA in Single and Multiple-Species Unsaturated Biofilms", Applied and Environmental Microbiology, vol. 71, No. 9, pp. 5405-5410, (Sep. 2005).

(56) References Cited

OTHER PUBLICATIONS

Stephenson, M.L., et al. "Inhibition of Rous sarcoma viral RNA translation by a specific oligodeoxyribonucleotide", Proc. Natl. Acad. Sci. USA, 75, No. 1, pp. 285-288 (1978).
Switzer, C. "The Existence of 2, 4-D—Resistant Strains of Wild Carrot", Proc. of the North Eastern Weed Control Conference, vol. 11, pp. 315-318, (1957).
Sykes, K.F. et al., "Genetic Live Vaccines Mimic the Antigenicity but Not Pathogenicity of Live Viruses", DNA and Cell Biology, vol. 18, No. 7, pp. 521-531, (1999).
Torsvik, V et al., "High Diversity in DNA of Soil Bacteria" Applied and Environmental Microbiology, vol. 56, No. 3, pp. 782-787 Mar. 1990.
Waites, M.J. et al., "Microbial Biomass Production", Industrial Microbiology: An Introduction. Blackwell Science Ltd., p. 218, (2001), 3 pages.
Wakelin, AM et al., "A Target-Site Mutation is Present in a Glyphosate-Resistant Lolium Rigidum Population", Weed Research, 46, pp. 432-440, (2006).
Whitchurch, C. et al., "Extracellular DNA Required for Bacterial Biofilm Formation", Science, vol. 295, p. 1487, (Feb. 22, 2002).
Whitehead, C.W. et al., "The Differential Response of Strains of Wild Carrot to 2, 4-D and Related Herbicides", Canadian Journal of Plant Science, vol. 43, No. 3, pp. 255-262, (Jul. 1963). 9 pages.
Written Opinion for International Application No. IT NA20120046 filed Aug. 2, 2012 on behalf of No Self S.R.L, dated May 17, 2013. 6 pages.
Written Opinion for International Application No. PCT/IT2013/000193 filed Jul. 10, 2013 on behalf of No Self S.R.L, dated Mar. 21, 2014. 11 pages.
Zamecnik, P.C. et al., "Inhibition of Rous Sarcoma Virus Replication and Cell Transformation by a Specific Oligodeoxynucleotide", Proc. Natl. Acad. Sci. USA, vol. 75, No. 1, pp. 280-284, (Jan. 1978).
Angiosperm Phylogeny Group (AGP), "An update of the Angiosperm Phylogeny Group classification for the orders and families of flowering plants: APG III," Botanical Journal of the Linnean Society 161(2): 105-121, (Oct. 19, 2009). 17 Pages. DOI: 10.1111/j.1095-8339.2009.00996.x.
Bergomaz, R., et al., "A simple instant diet for rearing Arctiidae and other moths," Journal of the Lepidopterists' Society, vol. 40, issue 3. (1986). pp. 131-137. 7 Pages.
Bonanomi, G., et al., "Phytotoxicity, not nitrogen immobilization, explains plant litter inhibitory effects: evidence from solid-state 13C NMR spectroscopy," New Phytologist, 191: pp. 1018-1030. (May 17, 2011). 13 Pages.
Camacho, C., et al., "BLAST+: architecture and applications," BMC Bioinformatics. 10(1), 421. (Dec. 15, 2009). 9 Pages.
Cao, J., et al., "Effects of Mg2+ on the growth and DNase activity of *Spirulina platensis*, a cyanobacterium," Bioresource Technology, 67(3), pp. 287-290. (Mar. 1999).
Dunahay, T.G., "Transformation of microalgae using silicon carbide whiskers," Recombinant Gene Expression Protocols, Humana Press. (1997). pp. 503-509. 7 Pages.
Examination Search Rpt for Canadian Application No. 2,880,411, Examination Search Rpt, dated Nov. 2, 2021, 1 page.
Fulton, T.M., et al., "Microprep protocol for extraction of DNA from tomato and other herbaceous plants," Plant Molecular Biology Reporter 13 (3), pp. 207-209. (Sep. 1995).
International Preliminary Report on Patentability for International Application No. PCT/NL2020/050086 filed on Feb. 14, 2020 on behalf of Koppert B.V, dated Aug. 10, 2021. 8 Pages.
International Search Report for International Application No. PCT/NL2020/050086 filed on Feb. 14, 2020, on behalf of Koppert B.V, dated Apr. 1, 2020. 4 Pages.
Laha T., et al., "The bandit, a New DNA Transposon from a Hookworm—Possible Horizontal Genetic Transfer between Host and Parasite," PLoS Negl Trap Dis 1(1): e35. (Sep. 27, 2007). 11 Pages, doi.org/10.1371/journal.pntd.0000035.
Mazzoleni, S., et al., "Inhibitory and toxic effects of extracellular self-DNA in the litter: a mechanism for negative plant-soil feedbacks?" New Phytologist, vol. 205, No. 3, Oct. 29, 2014. pp. 1195-1210,XP055601496, GB ISSN: 0028-646X, 16 Pages.
New Biological Books, Dec. 1979, p. 463. Section: Zoological Sciences. A description of The Genetics and Biology of *Drosophila*. vol. 2.
Smit, A.F., et al., "The origin of interspersed repeats in the human genome", Current Opinion in Genetics and Development, vol. 6, Issue 6, Dec. 1996, pp. 743-748. RepeatMasker. URL: www.repeatmasker.org.
Written Opinion for International Application No. PCT/NL2020/050086 filed on Feb. 14, 2020, on behalf of Koppert B.V, dated Apr. 1, 2020. 7 Pages.
Zang, X., et al., "Optimum conditions for transformation of *Synechocystis* sp. PCC 6803," The Journal of Microbiology, 45(3), pp. 241-245. (Jun. 2007). 5 Pages.
Third Office Action for Chinese Application No. 201710993629.4 filed on Jul. 10, 2013 on behalf of No Self SRL, dated Dec. 10, 2021. Original and English Translation. 14 pages.

| *Sarcophaga carnaria* | t = 0 | t = 10 days | t = 20 days | number of living flies |
|---|---|---|---|---|
| Control | | | | 25 |
| heterologous DNA (200 ppm) | | | | 24 |
| self DNA (20 ppm) | | | | 2 |
| self DNA (200 ppm) | | | | 0 |

Fig. 6

Experimental evidences of DNA accumulation in bioreactor supernatant and related inhibiting effect on the growth A  *Bacillus subtilis*

B  *Saccharomyces cerevisiae* fluorescence of supernatant from microbial cultures on 1% agarose gel + SYBR safe

C

| | |
|---|---|
| 1 | - |
| 2 | TUBE FOR SATURATED MEAN TAKING |
| 3 | PUMP FOR SATURATED MEAN TAKING |
| 4 | EXTERNAL REMOVAL UNIT |
| 5 | TUBE FOR SEPARATED NUCLEIC ACID |
| 6 | PUMP FOR SEPARATED NUCLEIC ACID |
| 7 | TUBE FOR CLEANSED MEAN RECICLE |
| 8 | PUMP FOR CLEANSED MEAN RECICLE |
| 9 | - |
| 10 | - |
| 11 | - |
| 12 | CHECK ELECTRONIC OF THE FIELD |
| 13 | METAL PLATES |
| 14 | ELECTRIC FIELD |

| | |
|---|---|
| 1 | - |
| 2 | TUBE FOR SATURATED MEAN TAKING |
| 3 | PUMP FOR SATURATED MEAN TAKING |
| 4 | EXTERNAL REMOVAL UNIT |
| 5 | TUBE FOR SEPARATED NUCLEIC ACID |
| 6 | PUMP FOR SEPARATED NUCLEIC ACID |
| 7 | TUBE FOR CLEANSED MEAN RECICLE |
| 8 | PUMP FOR CLEANSED MEAN RECICLE |
| 9 | - |
| 10 | - |
| 11 | - |
| 12 | - |
| 13 | - |
| 14 | - |
| 15 | MAGNETIC FIELD |
| 16 | PERMANENT MAGNET/ELECTROMAGNET |

17 WATER PUMP
18 FERTILIZER SOLUTION TANK
19 NUCLEASE SOLUTION TANK
20 MAIN FLOW TUBE
21 INJECTION LINE OF FERTILIZED SOLUTION
22 INJECTION LINE OF NUCLEASE
23 HEAD TUBE
24 DRIPPING WINGS OR LINES,
25 DRIPPERS OR SPRINKLARS
26 IRRIGATED AREA

COMPOSITION COMPRISING NUCLEIC ACIDS OF PARASITIC, PATHOGENIC OR INFESTING BIOLOGICAL SYSTEMS FOR INHIBITING AND/OR CONTROLLING THE GROWTH OF SAID SYSTEMS AND PROCESS FOR THE PREPARATION THEREOF

CROSS REFERENCE TO RELATED APPLICATIONS

The present application is a continuation of U.S. application Ser. No. 14/418,337 filed on Jan. 29, 2015, which, in turn, is the US national stage of International Patent Application PCT/IT2013/000193 filed on Jul. 10, 2013 which, in turn, claims priority to Italian Patent Application NA2012A000046 filed on Aug. 2, 2012, the content of all of which are incorporated herein by reference in their entirety.

The present invention concerns nucleic acid compositions of parasitic, pathogenic and infesting biological systems for inhibiting and/or controlling said systems and process for preparation thereof. Further the invention concerns a process and related system allowing the improvement of the production/growth of microorganisms at high yield in bioreactors or photobioreactors, or plants in various culture systems, by separation of nucleic acids produced by said organisms.

DESCRIPTION

Background of the Art

Since many years, the research for new products inhibiting biological systems demands an enormous scientific, economic and industrial effort and includes the detection of active principles from natural sources or by synthetic way and successive biological and pharmacological tests, both in vitro and in vivo, in addition to field and clinical application tests (Morgan et al. 2011. Health Policy, 100:4-17).

The drug use (pesticides, herbicides, antibiotics) for the inhibition of biological systems concerns various fields of application, among which there are mainly agriculture and medicine and it is finalized to the control, inhibition or elimination of harmful organisms, whether pathogenic, parasitic, or infesting, and also treatment against the formation of microbial biofilms.

In spite of the wideness and diversification of such application range, the use of drugs displays shared problems as (i) the specificity of action, (ii) the possible toxicity for human and other species, (iii) the environmental contamination and (iv) the onset of resistances in the populations of the target organisms.

Generally the drugs (pesticides, herbicides, antibiotics) consist of small and middle size organic molecules and display a large diversification both in terms of chemical components and action mechanisms. Such drugs have been detected generally based on methods of "random screening", that is estimating the activity and the use potentiality of chemical compounds obtained by synthesis in random way starting from various basic structures resulting from naturally occurring backbones. Accordingly in the course of the last 50 years, a very large number of products, among which more recently also polynucleotides, were marketed.

One of the main problems related to the currently active principles used in agriculture and medicine is not sufficient action specificity thereof for the parasitic, pathogenic and/or infesting organisms and consequently side effects and toxicity on the host organism. For example are known the cases of Paraquat associated to the onset of the Parkinson's disease and products proved to be lethal for human embryos. In addition to the problems of acute toxicity, the chronic exposure to some products displays a recognized risk for cancerogenicity, for which the enforced norms demand for ecotoxicological monitoring and use modalities associated to environmental dynamics and persistence of the various products.

At last, it is not to be ignored the problem of the environmental contamination caused by drugs (pesticides, herbicides, antibiotics). The recent applications of regulations in environmental field have drastically reduced the authorizations to the use of phytodrugs and pesticides and many products will have to be abandoned in the near future for the entering into force of more restrictive regulations. For example, methyl bromide, widely used as fumigant for the control of pathogens in the soil, among which nematodes, has been prohibited due to the inclusion thereof among compounds considered responsible for damage to the ozone layer. Taking into consideration these problems, the majority of more modern active principles were selected for a fast decomposition thereof in the soil or crops. However, this possible advantage in terms of environmental contamination can limit the effectiveness over the time of the used active principles.

Another shared fundamental problem for currently used products, both in agricultural field and therapeutic applications in medical field, is the appearance of pharmacological resistance after a period from the starting of the treatment.

For example, with reference to agriculture, in USA, in the early sixties, 2,4 D has been the first herbicide, used on wide scale, for which the onset of resistance in populations of *Dacus carota* was reported (Switzer, (1957), Proc. North Eastern Weed Cont. Conf., 11:315; Whitehead and Switzer, (1963), Can. J. Plant Sci., 43:255). Successively, starting from early '70 years numerous cases of infesting species resistant to triazines (Ryan, (1970), Weed Sci., 18:614; LeBaron and Gressel, Eds., Herbicide Resistance in Plants, Wiley, N.Y., 1982) were reported. The records then has grown exponentially in the following decades together the diffusion of the new products for chemical and biological fight and intensive use thereof (Powles and Shaner, 2001. Herbicide resistance and world grains, CRC press, New York).

Various onset mechanisms of infesting resistance to herbicide treatment are known. For example, various mechanisms reported in literature are: resistance as a result of selection of multiple copies of target genes (Gaines et al. 2010, Proc. Natl. Acad. Sci. 107(3): 1029-1034); mutation of the target genes (Wakelin et al. 2006. Weed Res. (Oxford), 46(5): 432-440); vacuolar sequestration (Ge et al. 2010. Pest Management Sci. 66:576); expression of enzymes that metabolize the herbicides (Hidayat et al. 1997. Pest. Biochem. Physiol. 57(2): 137-146).

Currently in the agricultural field, the appearance of resistance in over 200 infesting species was detected, selected above all as a result of the use of active principles characterized by the same mechanism of action. In Italy, in Po plain, cases of resistance to Atrazines in populations of infesting herbs are known, like *Solanum nigrum, Chenopodium album* and *Amaranthus cruentus*, or, in other regions, those with resistance to enzymatic inhibitors in different other infesting species (*Lolium* spp, *Phalaris paradoxa, Papaver rhoeas, Sinapis arvensis, Echinocloa crusgalliums, Sorghum halepense, Cyperus difformis*).

Also in medical field, the development of resistance to drugs makes useless the use thereof, constituting one of greatest problems related to antibiotic therapies (Clatworthy et al. 2007. Nat. Chem. Biol. 3(9): 541-548). Although enormous human and economic resources in order to discover new molecules and to study the resistance mechanisms were used, the appearance of the resistance to drugs proved to be faster than the discovery of new drugs.

The problem of the drug-resistance became primary world-wise in the field of health as it results in clinical complications for the antibiotic therapy (increase of the duration of diseases, increase of complications, possibility of epidemics) and demands for additional costs in the treatment of the infections from antibiotic-resistant bacteria (by means of use of further drugs, thus lengthening of the hospitalization). A case of antibiotic-resistance, more and more present and dangerous for the public health and representing one of the main causes of hospital infections, is meticilline resistance of the staphylococci and above all of various strains of Staphylococcus aureus. These bacteria, by means of the mechanism of reduced affinity for the target, are able to express a modified protein that does not interact with beta-lactam antibiotics. The European Union has faced this problem presenting a "Communitarian Strategy against the Antimicrobial Resistance" wherein a prudent use of antimicrobial agents in medicine is recommended in order to contain the development of resistances.

The possibility to inhibit the expression of specific genes resulted in great interest since the first publication of Zamecnik and Stephenson paper wherein it is shown that the use of compositions based on antisense oligonucleotides (ASO) could inhibit the viral protein translation (Zemecnik and Stephenson (1978) Proc. Natl. Acad. Ski. 75:285-288). Following this discovery, the most recent experimentations on techniques of fight to parasitic, pathogenic and infesting agents further investigated about the use of various RNA and/or DNA small size molecules (in the order of various tens of bases) selectively binding to targets displaying complementary sequences like mRNA, microRNA, or mitochondrial RNA, thus inhibiting the translation thereof and therefore carrying out a control activity for the targeted species.

These modern methodologies found applications in the fight against parasitic species (e.g. WO 2005/049841 A1), infesting plants (e.g. WO 2011/11257 A1) and antimicrobial and oncologic therapy.

The currently used approaches are multiple, among which the modification of RNA in order to control the level of specific RNA messenger thus limiting the expression of the gene encoding the same. Such methodology is characterized by the administration by means of suitable constructs of a RNA or DNA sequence aimed to a specific target, for example a gene or parts thereof. The problems associated to the use of such therapeutic approaches include the necessity of characterization for a specific sequence as therapy target. There is also the difficulty to obtain an effective minimal concentration of the construct in the target organ. The recent history of the antisense technology, in addition, reveals that while the identification of ASOs binding specific RNAs is now relatively simple, formulation thereof in compositions displaying an effective application potentiality for the inhibition of the expression of specific genes being still problematic. Various recent studies addressed aforesaid problem, proposing more stable and effective structures and compositions (e.g. WO 2011/031520 A1). As it is well-known this type of techniques displays elevated selectivity in terms of specificity of the action site. Up to now cases of the onset of resistance to the use of ASOs in herbicide and pesticide treatment are not reported as their application has not still reached the stage of commercialization and consequent dissemination of the products. However, taken into consideration the particular action specificity of the ASOs, it is realistic to presume that, as a result of extensive use thereof and consequent selective pressure on the infesting, parasitic and/or pathogenic populations, the application of said ASOs will result in the onset of resistances in the treated populations thus making ineffective the treatments, in the same way as it occurred in the past for other drug types characterized by elevated specificity of action.

In the field of the bulk cultures in bioreactors and photobioreactors, therefore in confined controlled systems, one of not yet solved major problems in the bulk culture of microorganisms is the onset of saturation phenomena of the growth curve for said organisms (stationary stage), with consequent impossibility to exceed certain concentrations for volume unit. A typical growth curve of such microorganisms (bacteria, photosynthetic bacteria, yeasts, microalgae and blue-green algae) is characterized by a starting latency stage, a successive exponential stage and a steady-state stage with saturation of the growth curve, followed sometimes also from a cellular death stage.

The impossibility to exceed the threshold of the maximum concentration for volume unit that a microorganism can reach during the culture on large scale in reactors and systems of bulk culture, remarkably limits the potentialities of exploitation of such organisms not allowing ulterior increments of the production beyond the stationary stage.

Various motivations are proposed as cause of the decrease of the cell growth rate of the microorganisms in saturation stage, all mainly related to the limitation of nutritive elements in medium, or auto-limitation of the culture penetrating radiation in the case of photosynthetic organisms (self-shading phenomenon). Various experimental studies demonstrated that the phenomena of the growth curve saturation occur as well in the absence of apparent limiting factors and this phenomenon is associated with accumulation of inhibiting substances in culture medium.

In the light of above exposed it is therefore apparent the need for new methods for the inhibition of harmful organisms or the increase of yield in the production processes of microorganisms overcoming the disadvantages of the prior art methods.

The title invention results from an important observation occurred during ecological studies on the cycle of the organic substance in the soil. In these studies it was observed that the DNA, released by the decomposition of soil accumulated organic material, proves to be inhibiting for the plant species producing said organic material, meanwhile said DNA does not inhibit other species for which said DNA can on the contrary represent a nutritive resource.

In the case of forest ecosystems this inhibiting effect of specific extracellular DNA only on species of plants with homologous DNA, represents a regulating mechanism of the natural co-existence among various species and favours the biodiversity of plant communities. In fact, when a single species, for any reason, is under conditions suitable to increase the own dominance on other species, in the time, necessarily, will accumulate larger residues of self organic substance, whose decomposition and consequent DNA release will produce an inhibiting effect on the same species thus reducing the competitive ability and therefore the dominance. On the same phenomenon is based the so-called "fatigue of the soil" (either referred as "soil sickness") in agriculture, that is productivity losses of the repeated monospecific cultures in the time not resulting from nutritive nature problems, but from accumulation of plant residues of the same cultures. The observation of species-specific inhibition due to accumulation of self DNA, during the cycle of the organic substance, explains the aforesaid phenomena of productivity loss and said finding never was reported in the scientific literature.

On the base of these studies, a second important result was reached, consisting of the observation that microbial populations (for example bacteria, microalgae and fungi) produce and secrete, during the growth, self DNA molecules in form of different size fragments which, by accumulation in the population growth substrate, exert a inhibiting effect on the growth of said population.

It is known that a microbial population typically grows initially in exponential way then enters in a so-called stationary stage, followed, possibly, from a death stage. Various growth limiting factors of such microbial populations are known, among which, fundamentally, the nutritive limits and/or accumulation of toxic substances of various nature. In literature it is reported the production and secretion of extracellular DNA from various organisms (Peters and Pretorius, 2011. Chemical Clinic Acta. 412:806-811), but up to now it is not reported that an extracellular DNA release during the growth of a microbial population produces an inhibiting effect on the growth of said population, in absolutely analogous way as observed for the plants affected by the accumulation of self DNA in the soil. The observations this invention is based on reveal a general, biological law according to which the release of self DNA by an organism proves to be regulating the growth of said organism and of the same species population organisms. This result leads to new remarkable application scenarios in agro-pharmaceutical field. Particularly, the control of any harmful species becomes possible through the exposure to self total, random fragmented DNA, such to reproduce what observed in the natural cycles of decomposition of the organic substance or in the extracellular secretion phenomena during the growth of the microbial populations. Thus it is hypothesized a possible application use of compositions whose active principle consists of total and random fragmented DNA of a to be controlled species.

The tests that are illustrated below demonstrate the effectiveness of such method for any treated species. Those reported are easy replicable experiments and do not demand any a priori knowledge of the genome of the to be treated species in terms of sequencing and/or detection of specific target genes. For the preparation of the inhibiting compositions only the extraction of the total DNA from organic material of the target species (for example from leaves of plants, fungus mycelium, microbial biomass) and successive random fragmentation of said extracted DNA are sufficient. The inventive set up procedure simulates the process of natural decomposition of the organic substance in the soil and produces a mixture of variously sized polynucleotides comprising from tens to thousands of bases. Such fragments, representing the total DNA of the to be controlled species, produce highly selective effect on organisms with homologous DNA whereas not act on a single target gene as it occurs, on the contrary, in the case of the various types of antisense oligonucleotides. This aspect potentially constitutes a remarkable advantage because it eliminates the possibility of appearance of resistances in the treated populations, because for no organism it is presumably possible to develop simultaneously resistances to the inhibition of all self functions. It is known, in fact, according to the scientific literature, that the onset speed of resistance phenomena in populations of parasitic, pathogenic and infesting agents is closely correlated to the number of genes responsible for such resistance. More precisely, lower the number of necessary genes for the resistance onset, greater the speed according to which this resistance will be positively selected inside of the to be controlled population (Prather et al. the 2000. Herbicide resistance: definitions and management strategies. University of California, Division of Agricultures and Natural Resources, Oakland—Brent and Hollomon, 2007. Fungicide resistance in crop pathogens: how can it be managed? Croplife International, Brussel).

The invention concerns therefore the use of compositions for inhibiting parasitic, pathogenic and/or infesting species wherein, like active principle, random fragments of total self DNA, identical or similar to the same genome of the to be inhibited species are used. Further the present invention concerns a composition comprising said random fragments of total DNA.

In addition the inventors of the present invention developed a process and the related system for the production/growth of microorganisms in bioreactors or photobioreactors or plants in systems for hydroponic culture, on substrates outside the soil, or in soil, by means of separation of nucleic acids of said microorganisms or plants.

Below in the present patent application, the term "saturation level" means that stage established in the course of growth of the microorganisms, when the concentration of nucleic acids or fragments thereof in culture medium is such to result in a steady-state stage regarding the course of growth of the microorganisms, with saturation of the growth curve thereof. In the same way, the term "exhaust medium" means a culture medium wherein the level of concentration of nucleic acids and fragments thereof reached a concentration resulting in a saturation level on the growth course of the microorganisms.

As to the term "reclamation" it means the operation suitable to remove nucleic acids and fragments thereof from exhaust medium.

"Regenerated medium" means medium obtained after the reclamation of exhaust medium.

DETAILED DESCRIPTION OF THE INVENTION

The present invention is based on the experimental evidence that the exposure of an organism to extracts of total self DNA results in an inhibiting effect on the functions of said organism, thus limiting the growth or interfering in fundamental way with physiology thereof at cellular level. In detail, the total DNA of a parasitic, pathogenic and/or infesting organism extracted and administered without no selection of specific fragments or use of specific constructs, can be used as inhibiting product for the same organism or other organisms with identical or similar genome. The inhibiting action is exerted when the parasitic, pathogenic and/or infesting species is contacted, within growth substrate thereof or at systemic level, with randomly fragmented total self DNA. Once absorbed, such DNA produces a limiting effect on the growth and a generalized inhibiting effect on the various functionalities of the organism, otherwise than it occurs in the case of applications of specific nucleic acid sequences aiming to "gene silencing" or "RNA interference" effects. The adsorption and the inhibiting activity depend on the concentration and fragmentation level of the nucleic acids the system is exposed to. A greater effect is pointed out depending on the fragmentation degree of used molecules (for example after sonication or following natural decomposition). Experiments were carried out using various average lengths of DNA fragments and the inhibiting effect proves to be more effective for fragment mixtures with higher length frequency of approximately 200 bases.

Specifically, the production of random fragments of total DNA extracted from various species according to illustrative experimentations was carried out with various approaches in order to demonstrate that the fragmentation technique does not influence the effectiveness of the inhibiting effect. Said fragmentation can be carried out by means of natural degradation (exposure to environmental factors), artificial degradation (by combustion, enzymatic or mechanical way), or by synthesis (methods for random amplification like DOP, that is by PCR with degenerated oligonucleotides).

The authors of the present invention carried out studies on plants, fungi, insects, yeasts, algae and protozoa. The results of such experimentation unequivocally demonstrated the general subsistence of the described inhibiting effect on any treated species.

In the case of the plants, the presence in aqueous solution of the total DNA of a species, obtained by simple extraction and randomly fragmented, also at low concentration, in contact with the roots of the same species, quickly produces radical necrosis, leaf chlorosis, interruption of the meristem activities and, when in contact with the seeds, suppression of the germination ability. On the contrary, the exposure of the roots and/or seeds of a species to solutions of randomly fragmented total DNA of different species does not produce noticeable inhibitions, also for exposures at high concentration, i.e. showing a highly species-specific effect. It is therefore apparent that the presence of randomly fragmented total DNA in a growth environment can carry out a selective inhibiting function on organisms with identical or similar genome not influencing other species. It is possible to find out this inhibiting effect both when the total DNA is artificially fragmented and inserted in the growth medium of the biological system and when the DNA is produced and secreted by said biological system during the growth thereof.

This therefore makes possible an action targeted only against the parasitic, pathogenic and/or infesting species, by treatments with formulations containing DNA specific for this species, with the enormous advantage that said molecules will display the inhibiting effect only on the target species, but not on the to be protected or other species, also in case of possible repeated exposures.

The same principle observed by the inventors of the present invention can be favourably employed in order to increase the yields of processes for production of microorganisms in bioreactors and photobioreactors, tanks for hydroponic culture and culture systems outside the soil. In fact, the inventors of the present invention, by means of laboratory tests using bioreactors for growth of algae, yeasts and bacteria, observed a supernatant accumulation of variously sized DNA fragments (approximately 50-800 bp) belonging to the same produced microorganisms, during the growth stages at increasing concentrations. It was observed that this accumulation occurs in the growth stages at increasing concentrations and that results in an inhibiting effect on the growth of said culture when in the bioreactors the steady-state stage and successive death stage are reached (FIGS. 11A and 11B).

The experimental tests pointed out that a self-inhibiting species-specific effect exists, as cultures of a given species display to be inhibited only by supernatants of cultures of the same species. Further it was observed that the removal of the DNA from the culture medium is suitable to remove the inhibiting effect allowing the growth stage to be restored and higher cell densities in bioreactors (FIG. 11C) and photobioreactors to be reached.

Analogously, in tanks for hydroponic cultures of plants, in the presence of decreasing production in absence of complete replacement of the circulating nutritive solution, it was observed an accumulation in the substrate of DNA of the cultured species. Also in this case, the removal of the accumulated DNA from the growth substrate allowed the productivity to be restored.

Taking into consideration these experimental results, therefore, it is possible to develop technological systems for the removal of DNA occurring in cellular cultures (bioreactors and photobioreactors), hydroponic culture tanks and in culture systems outside soil in order the productions to be optimized.

It is therefore a specific object of the present invention the use of a composition comprising or consisting of a mixture of total DNA fragments wherein said total DNA is randomly fragmented for the prevention and the treatment against at least one pathogenic, parasitic or infesting species of the plants or environment, wherein said total DNA is total DNA of said pathogenic, parasitic or infesting species, and/or at least one phylogenetically similar species, against which said prevention and treatment are directed. As above said, the fragment mixture according to the present invention is obtained by fragmentation of the total DNA extracted from said pathogenic, parasitic or infesting species against which said prevention and treatment are directed, without carrying out any selection of fragments, that is using all fragments obtained from the acid nucleic. Therefore according to the present invention randomly fragmented whole DNA, that is without carrying out any selection of specific and/or specifically sized sequences, is used. Fragments of said total DNA are obtained by means of random fragmentation of the extracted total DNA, or by means of random fragment synthesis starting from the total DNA. The substantial difference of the technique of the present invention compared to the "gene silencing" and "RNA interference" current techniques is that in the current state of the art the specific regions of to be used nucleic acids must be actively selected, whereas in the case of the technique of the present invention nor previous knowledge neither selection for the to be used specific sequences are necessary. Said total DNA can be extracted from said at least one pathogenic, parasitic or infesting species or artificially synthesised. The nucleic acid can be amplified and/or fragmented by means of chemical and/or physical type procedures and the obtained fragments possibly can be further amplified. The production methods of random fragments of total DNA include, for example, chemical, biochemical and molecular methods, sonication techniques, heat treatments and pyrolysis procedures. For example, following the extraction of total DNA from leaf tissue from *Arabidopsis thaliana*, the exposure of the seeds from the same species to such extract containing DNA in not fragmented form does not display significant inhibiting effects. Differently following a sonication treatments of the extract using a dipping sonicator for three or four cycles lasting three minutes at 80% power produces a mixture of variously sized random fragments with increasing inhibiting activity, in function of reached fragmentation degree, on the germination of *A. thaliana* seeds. The same mixtures of random fragments of total DNA extracted from *A. thaliana* did not display inhibiting effect on other treated species, as *Lycopersicon aesculentum* and *Avena sativa* (used as control biotest in this experiment). Analogous results were observed when the extract of total DNA was randomly fragmented with other above cited chemical-physical methods. Finally the same results are obtained exposing seeds of *A. thaliana* to mixtures of random fragments of the total DNA wherein said fragments were obtained by amplification of total DNA using DOP. The composition can be used as biocide, herbicide, fungicide, insecticide, acaricide, nematocide, antiprotozoic, algaecide, bactericide. The composition can be administered to said at least one pathogenic, parasitic or infesting species by surface contacting, cytotropic administration, systemic administration by means of, for example, injection, ingestion or inhalation, or adsorption. The composition can be formulated in a form, for dry or liquid treatments, selected in the group consisting of dispersion, for example in form of aerosol, suspension, wettable or soluble powders, emulsions in water or other solvents, dispersible granules, suspensions of microcapsules, emulsifiable concentrates, fluid pastes, macro emulsions, oil dispersions, baits. According to a particular embodiment, the nucleic acid random fragments can be engineered in vectors. The composition according to the present invention can comprise further pesticides selected from the group consisting of fungicides, insecticides, nematocides, miticides, artropocides, bactericidal, algaecides.

The invention concerns further a method for the prevention or treatment against at least one pathogenic, parasitic or infesting species of the plants or environment, said method comprising or consisting of the following steps of: a) extraction of the total DNA of at least one of said pathogenic, parasitic or infesting species against which said prevention and treatment are directed; b) production of random fragments of said total DNA in order to obtain a mixture of DNA random fragments; and c) contacting said mixture of random fragments with said pathogenic, parasitic or infesting species.

A composition comprising or consisting of a mixture of total DNA random fragments for the use in the prevention and treatment against at least one pathogenic, parasitic or infesting species of man or animal, wherein said total DNA is the DNA of said at least one pathogenic, parasitic or infesting species, against which said prevention and treatment are directed, is a further object of the present invention. Said total DNA random fragments can be obtained by degradation of the total DNA by means of chemical and/or physical methods, or by synthesis of random fragments of said total DNA. The composition according to the present invention can be formulated for dry or liquid treatments, or aerosol dispersion, in form of suspensions, wettable or soluble powders, emulsions in water or other solvents, dispersible granules, suspensions of microcapsules, emulsifiable concentrates, fluid pastes and macro emulsions, oil dispersions, creams, capsules and tablets. The administration routes include contact or surface, systemic and cytotropic treatments, by injection, absorption, ingestion and inhalation, as well as any other administration route useful to the application end. The composition according to the present invention can include mixtures with other chemical compounds acting as tackifying agents, wetting agents, suspending agents, excipients, amending agent and solvents, surface-active agents, as well as other substances useful to the application end. At last, the composition according to the invention can include other pharmaceutical compounds in formulations and mixtures of not antagonistic but possibly synergic media with the activity of the treatments. In such cases the combination of compounds generally will correspond to weight ratios from about 0% to 100%.

It is also a specific object of the present invention a process for high yield production of microorganisms in bioreactors or photobioreactors, or for culture systems of plants both inside and outside soil, characterized in that the nucleic acids from the same organisms produced by said process are removed from culture medium and the culture medium deprived of said nucleic acid can be used again in said process.

According to the process of the invention, the nucleic acids are removed from the culture medium or growth substrate using separation techniques selected from the group consisting of: external removal unit, preferably consisting of an external container and a system for generation of electric, or magnetic, or electromagnetic fields and at least one duct and at least one displacement means for the extraction of concentrated nucleic acids from the preceding system; integrated removal unit, preferably consisting of a system of generation of electric, or magnetic, or electromagnetic fields and at least one duct and at least one displacement means for the extraction of concentrated nucleic acids from the preceding system, the whole integrated within the same bioreactor; techniques applicable in situ and outside units, preferably centrifugation techniques; filtration techniques; treatments with DNAse and other degrading enzymes for nucleic acids; heat treatments; acidifying treatments Preferably, according to the process of the invention, said nucleic acids are removed from the culture medium by means of at least one external or bioreactor or photobioreactor integrated removal unit or systems for hydroponic culture using techniques selected from the group consisting of application of static electric fields, application of static magnetic fields, application of dynamic magnetic and/or electric fields, centrifugation, filtration, treatment with DNAse, heat treatment, acidifying treatment.

A system for production of microorganisms comprising at least one bioreactor or photobioreactor or system for hydroponic culture, at least one unit for nucleic acid removal external to said at least one bioreactor or photobioreactor or system for hydroponic culture is an ulterior aspect of the present invention, said unit for nucleic acid removal being connected to said at least one bioreactor or photobioreactor or system for hydroponic culture by means of at least one first duct and at least one first displacement means for the withdrawal of culture medium containing acid nucleic, and a at least one second duct and at least one second displacement means for the re-introduction in said at least one bioreactor or photobioreactor or system for hydroponic culture the culture medium from which the nucleic acids are removed; said system comprising further at least one third displacement means for the withdrawal of separated nucleic acid. Preferably said duct can be a tube. Said displacement means can be preferably a pump.

The reclamation of culture medium is realizable both continuously using treatments for removal of the DNA from culture medium during the growth stage and carrying out a treatment of exhaust medium when saturation stage of the cellular growth occurs.

The reclamation of culture medium can be carried out "in situ" directly in the bioreactors or photobioreactors using treatments with enzymes or other compounds active for the degradation of the DNA occurring in the supernatant of the cellular cultures, or using techniques for application of electric, magnetic or electromagnetic fields. The reclamation using these techniques proves to be viable taking advantage of the polarity characteristics of nucleic acid molecules therefore separable by electric fields, or using techniques for magnetization of DNA molecules by binding the same to magnetic molecules and applying magnetic fields for the separation thereof. Alternatively, the reclamation can be carried out using a removal system placed outside the bioreactor (FIG. 12 A) or hydroponic culture (FIG. 13A) with re-circulation of regenerated medium or a bioreactor (FIG. 12 B) or hydroponic culture integrated (FIG. 13B) removal system.

The techniques for removal of the DNA from culture medium can be: techniques for application of static electric fields (FIG. 14); techniques for application of static magnetic fields (FIG. 15); techniques for application of dynamic magnetic and/or electric fields; centrifugation; filtration techniques; treatment with DNase; heat treatments; acidifying treatment.

In a preferred embodiment of the invention (FIG. 12 A), said at least one bioreactor (1) can be connected to said at least one external removal unit (4) in such a way that the exhaust culture medium is transferred in at least said a removal unit (4) by means of at least one first duct (2) and at least one first displacement means (3) for the withdrawal of culture medium containing nucleic acid. In such unit (4), the reclamation can be carried out using one of the aforesaid techniques for DNA removal from medium. At this point the separated nucleic acid will be collected by the removal unit (4), preferably by means of at least one third duct (5) and at least one third displacement means (6) for the withdrawal of separated nucleic acid, whereas the regenerated medium will be re-introduced in said at least one bioreactor (1) by means of at least one second duct (7) and at least one second displacement medium (8).

Further the integration of the fertirrigation equipments in open field or protected culture with systems for removal of nucleic acids represents a further application of the present invention. A possible diagram of such application is reported in FIG. 16 wherein a tank with a solution containing nuclease is integrated in a fertirrigation equipment.

The use of total DNA random fragments for the control and inhibition the parasitic, infesting and/or pathogenic species in agriculture and medicine, compared to the existing techniques and products, results in significant advantages.

A first advantage results form the absolute selectivity of the treatments with total DNA random fragments of the parasitic, infesting and/or pathogenic species, because said total DNA random fragments do not display effects on species different than treated ones.

The use of total DNA random fragments of the parasitic, infesting and/or pathogenic species does not induce the appearance of resistance in the same species populations, because action mechanism thereof is different than that of the currently marketed or under experimentation products (including the methods of RNA interference and ASO), as based on a multiple and contemporary interference with the entire genome with the entire transcriptional and protein synthesis system, thus not allowing specific resistance and selection of resistant populations to be set up.

A further advantage results from the absence of toxicity caused from the nucleic acid use, that, being primary metabolites, ubiquitary in nature, do not result in environmental contamination. In fact, the administration of nonspecific nucleic acid fragments displays no toxicity for species other than treated ones.

The present invention affords further a remarkable simplification of the research for new drugs with consequent great economic benefit. In fact, the detection of parasitic, pathogenic and infesting species constitutes the only condition necessary for the preparation of the specific drug for the pharmacological treatment. On the contrary, the current pharmacological research for products based on techniques like RNA interference or use of antisense oligonucleotides, require not only the knowledge of the full genomic sequence of the target organism, but also the detailed knowledge of the gene functionalities in order to detect possible specific sequences to be targeted for inhibiting activity.

On the other hand, the traditional pharmacological research is based on "random screening" studies of synthetic compounds or naturally occurring molecules. Such substances, once detected and tested for their activity, in the majority of the cases are characterized also by a general toxicity for other organisms and humans. Practically, the application of such products often is associated to environmental contamination concerns due to the toxicity thereof.

A further advantage results from the relative easy availability and bulk production of nucleic acid meeting the requirements of title patent. In fact, random fragments of the total DNA of the target organism can be obtained by approaches and methodologies now extremely diffused in biomolecular field. The techniques can be based on extraction of the genetic material from the target organisms, or by means of synthesis.

Further, the stability of DNA fragments can assure the persistence over the time also under unfavourable environmental conditions (e.g. in the soil), resulting therefore, in durable applications resulting in both environmental and economic benefits.

A further advantage results from the fact that the DNA for the proposed uses can be obtained by extraction from naturally occurring material or by synthesis based on synthesis and extraction techniques and amplification as well, now widely diffused and established in molecular biology. Significant but not restrictive examples of possible production techniques include the dissolution of the cellular tissues, inactivation of the cellular nucleases and recovery of nucleic acids from the solution containing biological lysates.

Nucleic acids are further synthesizable starting from template molecules or de novo according to different approaches.

The considered molecules can be amplified, thus producing multiple copies identical or similar to the considered template, for example by cloning or PCR based techniques.

PCR variants are useful in order to produce the active principle to be used assuring random amplification of the nucleic acid fragments from a template sample. For example, an approach like Random Amplified Polymorphic DNA (RAPD) is very suitable to our end not requiring, otherwise than the classic PCR, knowledge of the starting DNA template sequence.

Emulsion PCR represents another example of innovative approach suitable to assure in an extremely quick way the amplification of various DNA fragments starting from a genomic DNA sample atomized so as to obtain 300-800 nucleotide long fragments, or from amplicons obtained by other approaches.

Further, as to the production processes of microorganisms in bioreactors and photobioreactors and tanks for hydroponic culture the removal of exhaust culture medium and the re-suspension of the cells in "regenerated" medium, at equal cellular concentration for volume unit and under the same contour conditions, allow the restoring of the culture growth stage.

In addition to the advantage of the production increase resulting from the removal of the inhibiting factor, a further remarkable advantage results from the possibility of re-use of exhaust medium, after regeneration thereof, for other successive cultures, possibility not viable in the current systems of production.

The present invention now will be described, illustrative, by an illustrative but not limitative way, with particular reference to embodying examples and enclosed drawings, wherein:

FIG. 6 shows the inhibition of *Sarcophaga carnaria* insect by exposure to self DNA.

Figure 11:
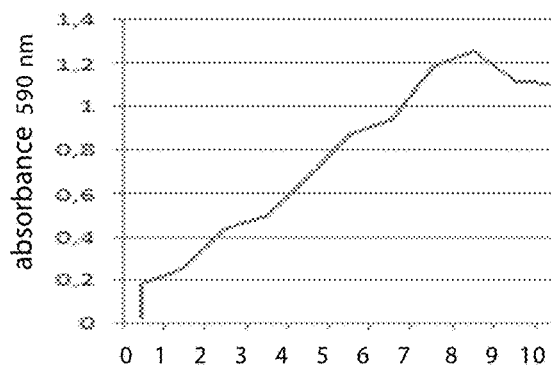
Figure 11:
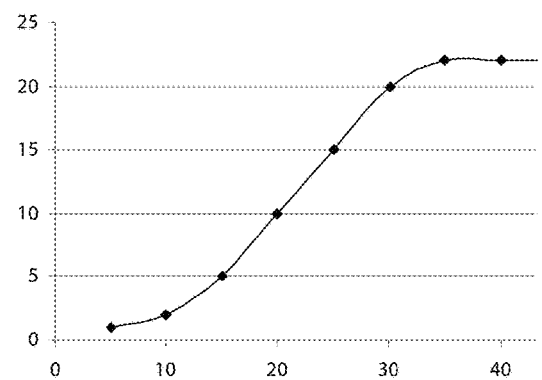
Figure 11:
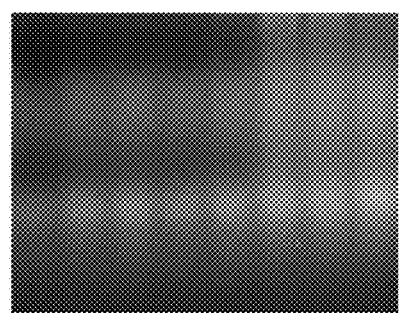
Figure 11:
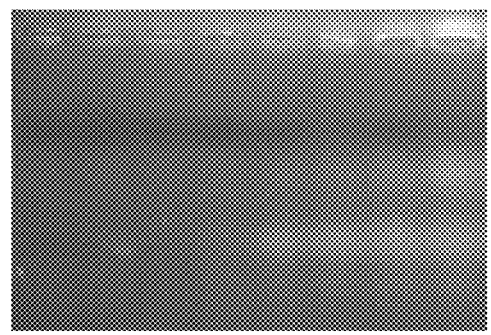
Figure 11:
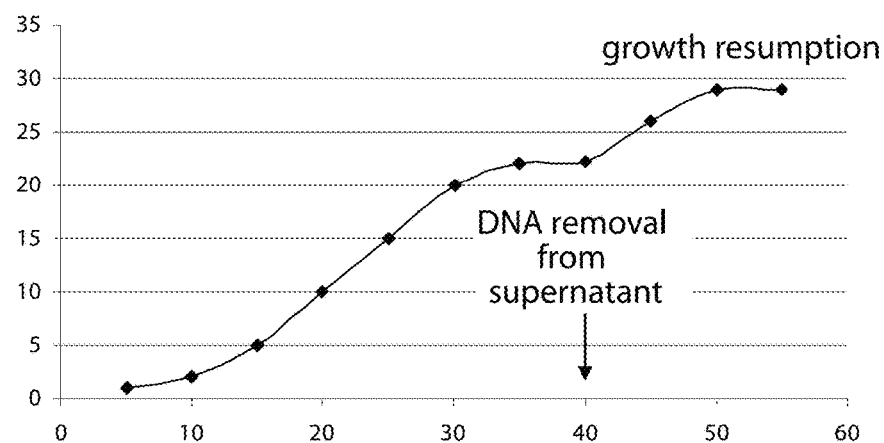

FIG. 11 shows the accumulation of extracellular DNA in the liquid substrate of two different bioreactors. Panel A of FIG. 11 shows fluorescence of supernatant from *Bacillus subtilis* culture on 1% agarose gel+SYBR safe. Panel B shows fluorescence of supernatant from *Saccharomyces cerevisiae* culture on 1% agarose gel+SYBR safe. Panel C shows *Saccharomyces cerevisiae* cell density in a bioreactor, wherein removal of the DNA from the culture medium is suitable to remove the inhibiting effect allowing the growth stage to be restored and higher cell densities.

Figure 12:
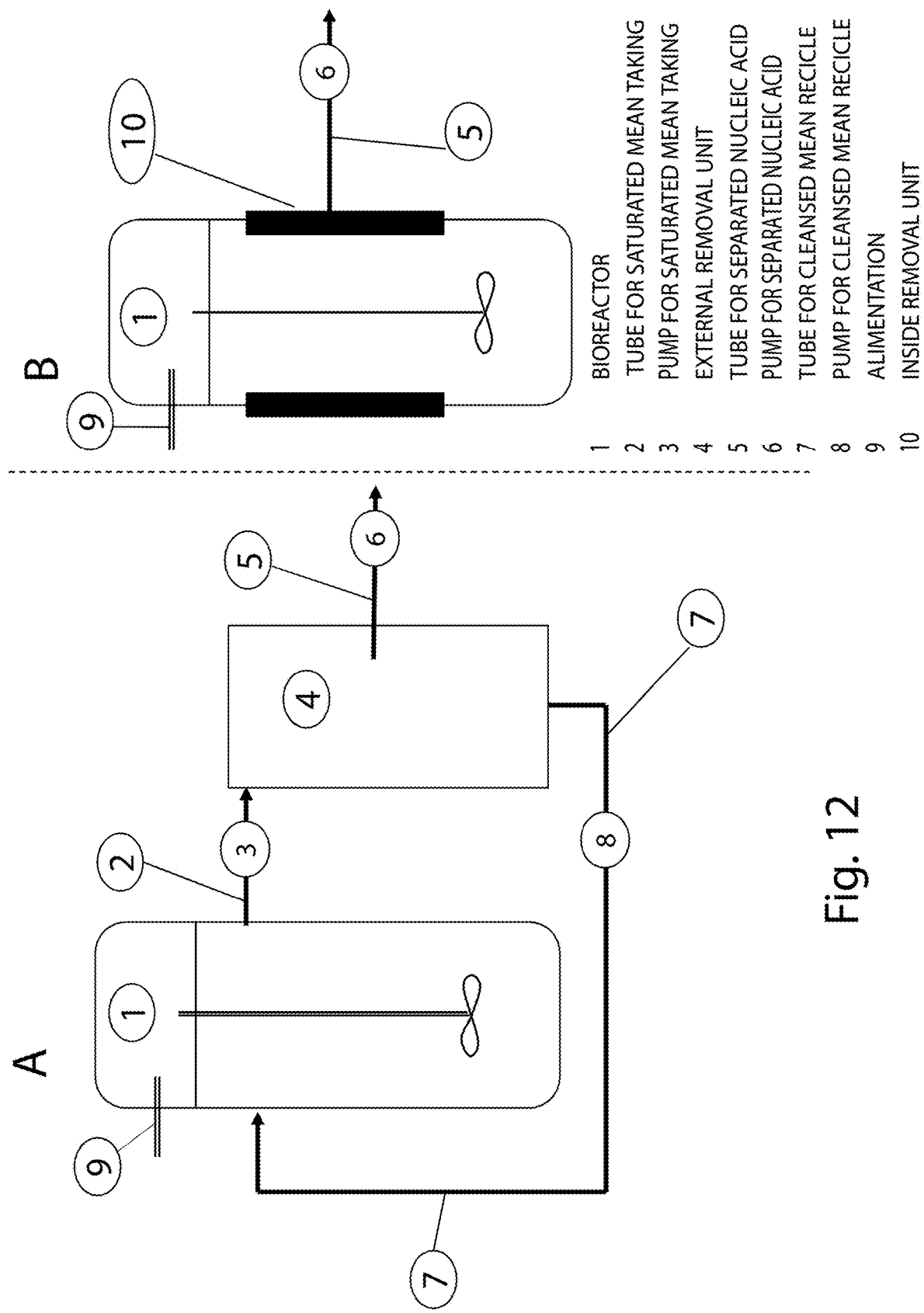

FIG. 12 shows: (a) the diagram of system for production of microorganisms in bioreactor characterized from an external unit for DNA removal; (b) the diagram of system for production of microorganisms in bioreactor wherein the removal of DNA from culture medium occurs by bioreactor integrated removal unit.

Figure 13:
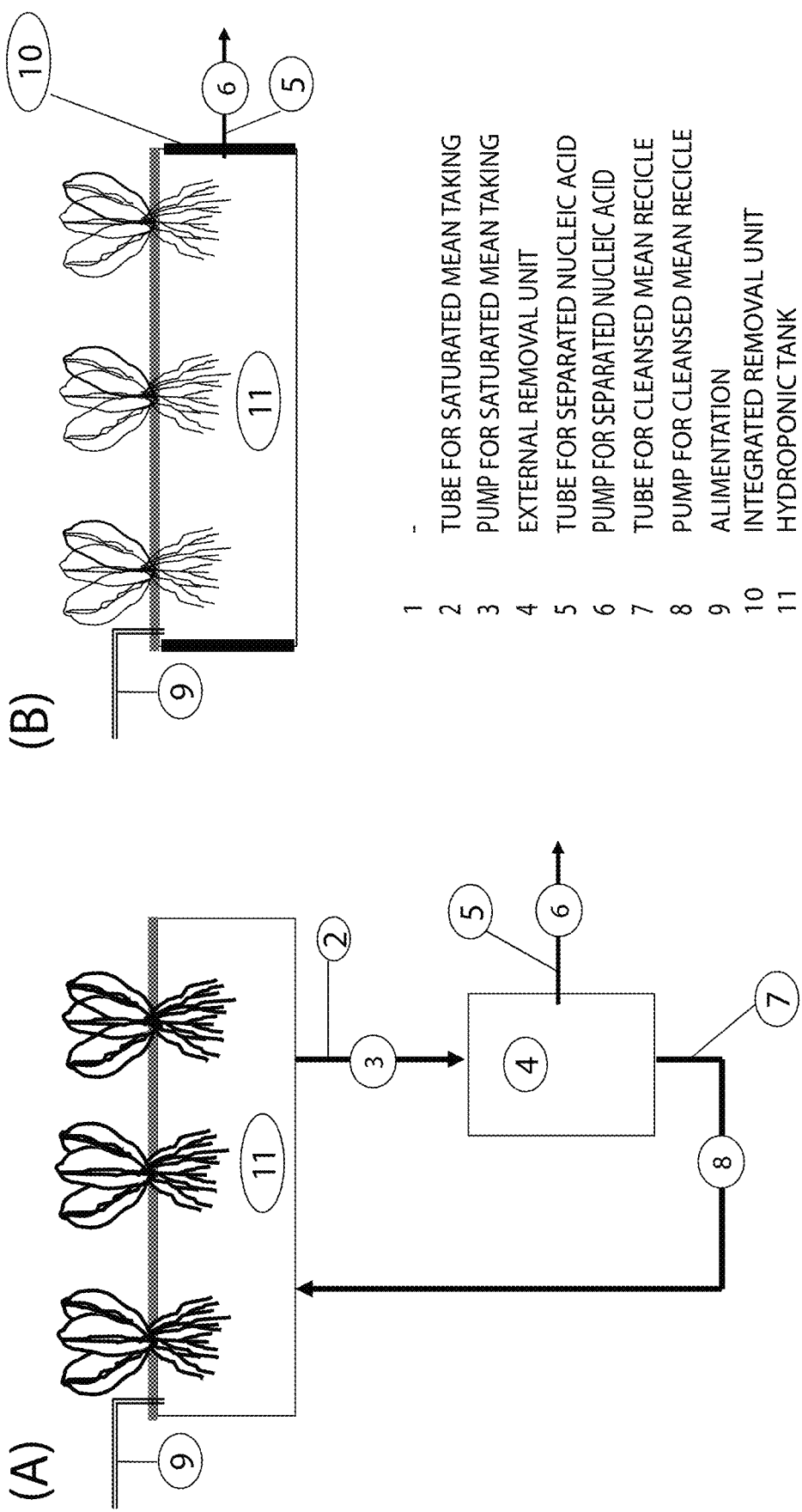

FIG. 13 shows: (a) a tank for hydroponic culture characterized from the presence of an external removal DNA unit and recirculation of culture medium within the hydroponic system; (b) a tank for hydroponic culture wherein the removal of the DNA from culture medium occurs by means of removal unit integrated to the same tank.

Figure 14:
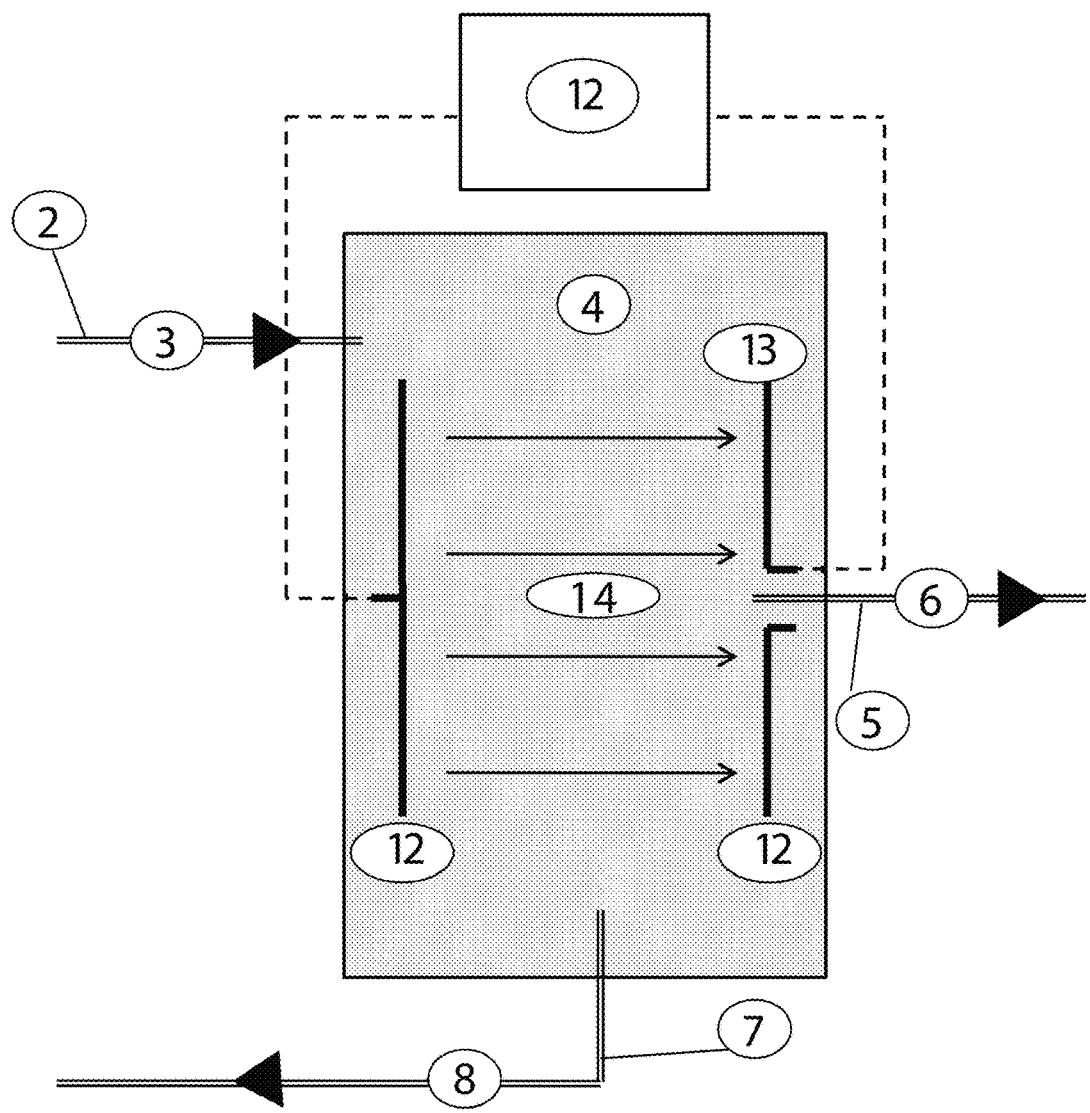

FIG. 14 shows a specific diagram of the external removal unit for the system represented in FIG. 12, wherein the separation of nucleic acid occurs by application of an electric field.

Figure 15:
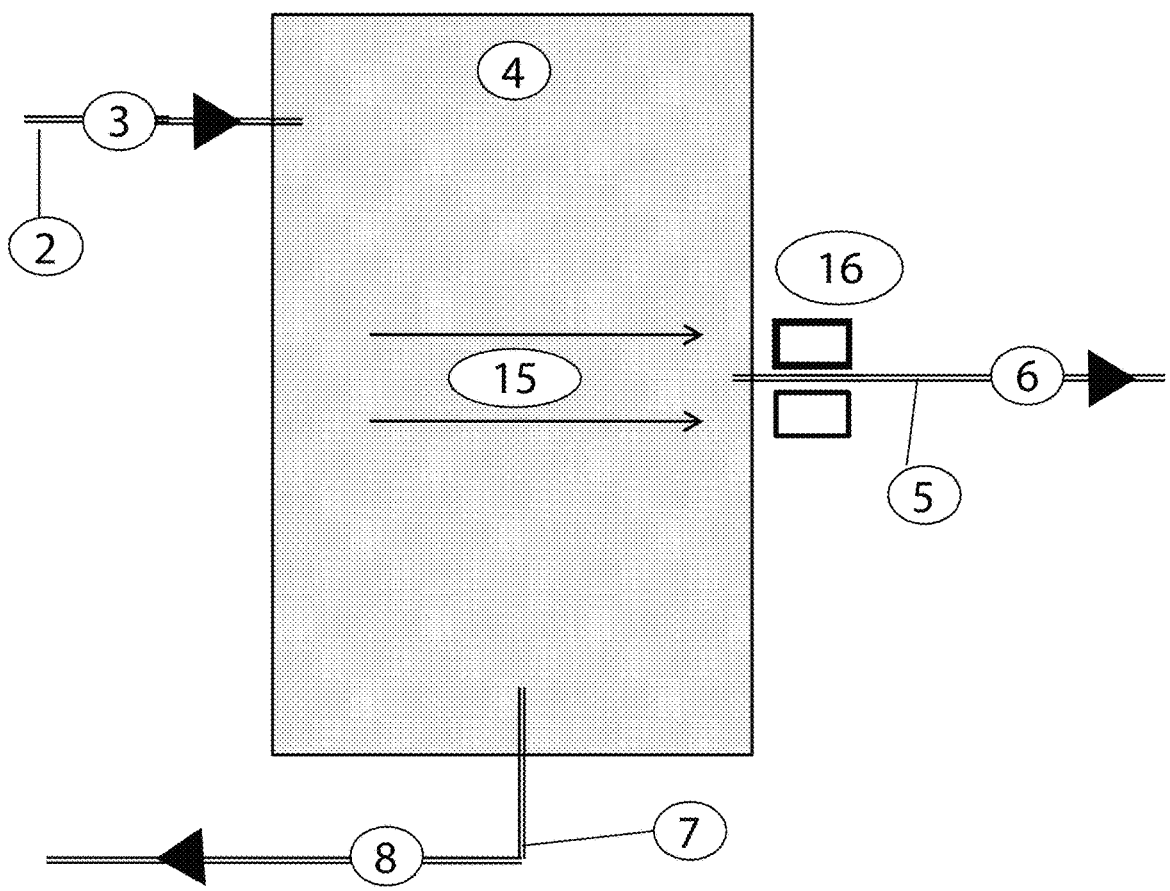

FIG. 15 shows a further diagram of the removal unit for the system showed in FIG. 12, wherein the separation of nucleic acid occurs by application of a magnetic field.

Figure 16:
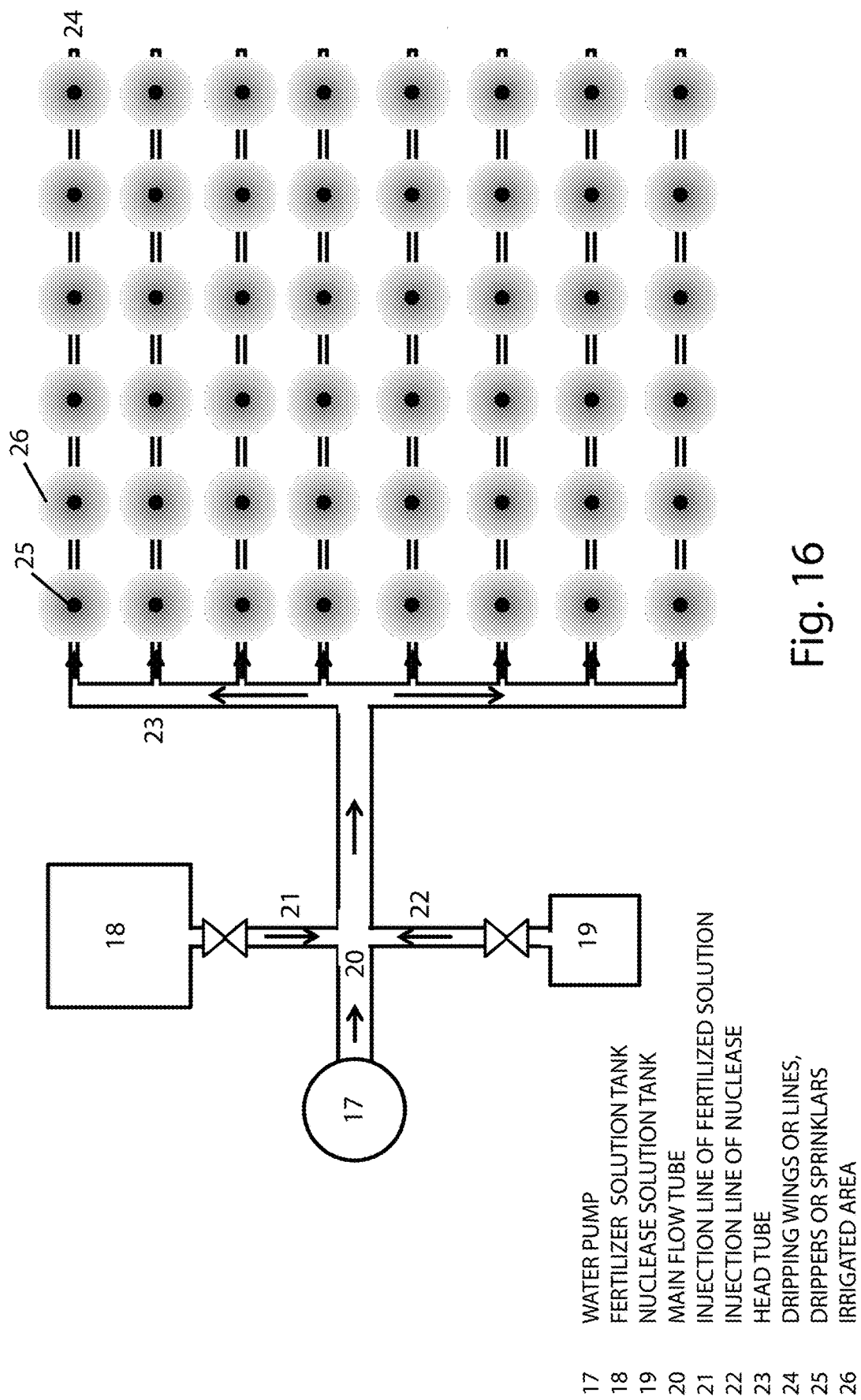

FIG. 16 shows an diagram of plant culture wherein the substrate is treated with nuclease by integration with fertirrigation system.

Figure 1:
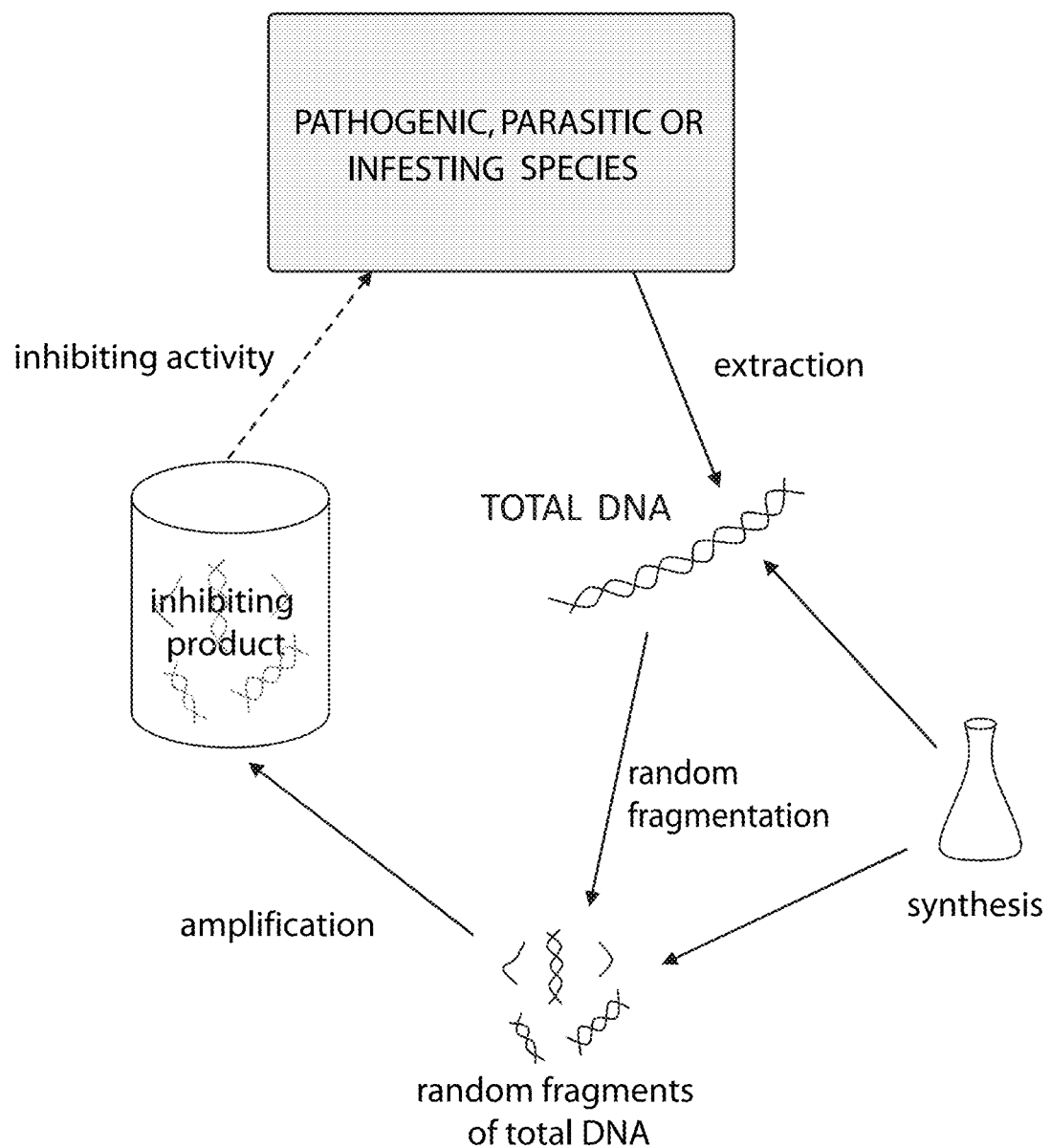
FIG. 1 shows a conceptual view of the object of the invention.

In all the examples of reported experiments, the nucleic acid composition used in the different treatments was prepared according to the procedure outlined in FIG. 1. In particular, the total DNA extracted with standard procedures from organic material (leaves, fungus mycelium, microbial biomass) was treated by sonication for at least three cycles lasting three minutes at maximum power with dipping sonicator until to obtain the production of composition of random fragments falling in 50 and 1000 bp size range. The verification of the fragmentation level is carried out by standard procedures using agarose or polyacrylamide gel electrophoresis and staining techniques, Sybr safe type and UV visualization.

Example 1

Inhibition of *Acanthus mollis* and *Lepidium sativum* Plants by Exposure to Self DNAs A first experiment was carried out on *Acanthus mollis* and *Lepidium sativum* plants, the latter species was selected because it is particularly sensitive to toxins. DNAs of acanthus, *Acanthus mollis*, and watercress, *Lepidium sativum*, were obtained by direct extraction from leaves of the two species and stored in distilled $H_2O$. Successively 10 previously sterilized seeds of *A. mollis* or *L. sativum*, in Petri plates (9 cm diameter) are placed on a sheet of sterile filter paper. The seeds of each species are treated separately with the DNA of the two species at concentrations of 2, 20 and 200 ppm whereas sterile $H_2O$ was added to the control. The germination of the two species and the total root length were quantified after 7 days of incubation at 24° C. by observation and measurement of the roots. Each treatment was repeated thrice.

Figure 2:
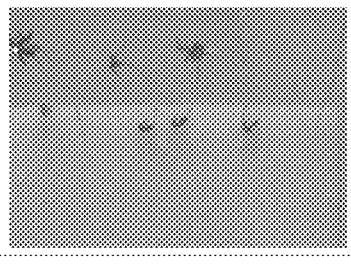
FIG. 2 shows the inhibition of the germination of seeds of *Lepidium* and *Acanthus* by exposure to self DNA at optimal concentration of 200 ppm.

The treatment of the seeds of the two species with DNA extracted from plants of the two species, applied separately, allowed to estimate the effect of the DNA on the root growth and the optimal activity concentration. The results of the experimentation, reported in FIG. 2, show that both seeds of *Lepidium* and seeds of *Acanthus* are inhibited in the germination by the exposure to self DNA at optimal concentration of 200 ppm. On the contrary, the exposure of seeds to DNA from other species does not show noticeable effects on the seed germination.

Example 2

Inhibition of *Quercus ilex, Quercus pubescens, Hedera elix, Ampelodesma mauritanica, Festuca drimeja, Coronilla emerus, Medicago marina, Alnus cordata, Robinia pseudoacacia, Pinus halepensis* Plants by Exposure to Self DNAs A second experiment concerned the analysis of the germination and root growth of 10 species of natural environment plants. Surface sterilized seeds of *Quercus ilex, Quercus pubescens, Hedera elix, Ampelodesma mauritanica,*

Figure 3:
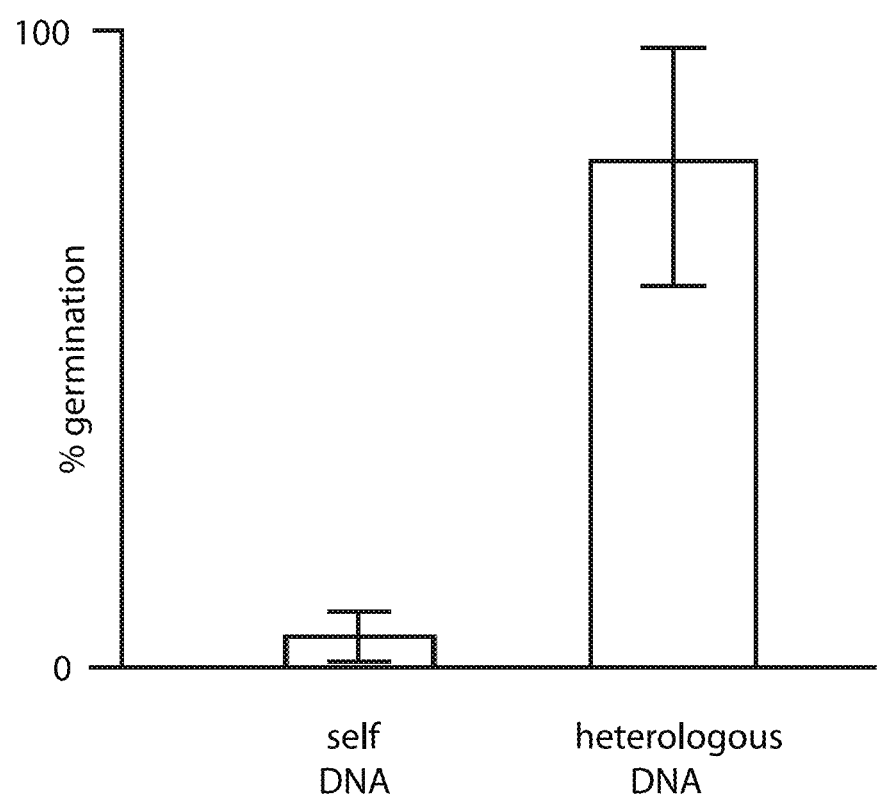
FIG. 3 shows the inhibition of *Quercus ilex, Quercus pubescens, Hedera elix, Ampelodesma mauritanica, Festuca drimeja, Coronilla emerus, Medicago marina, Alnus cordata, Robinia pseudoacacia, Pinus halepensis* plants by exposure to self DNA.
Figure 4:
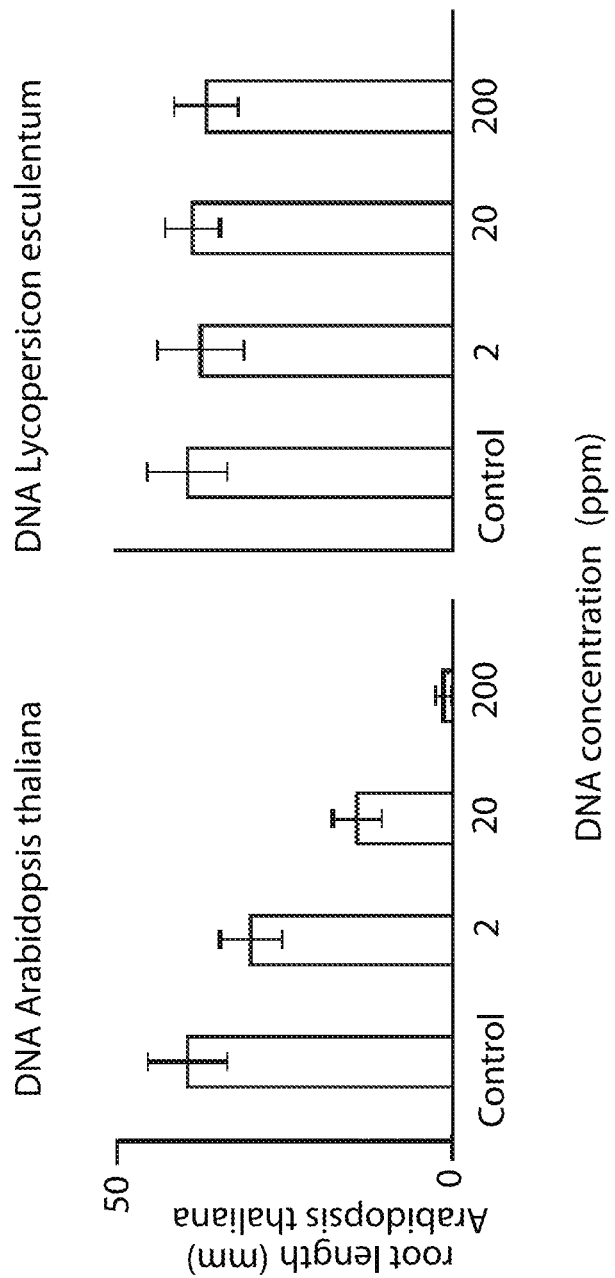
FIG. 4 shows the inhibition of *Arabidopsis thaliana* plants by exposure to self and *Lycopersicon esculentum* DNA.

*Festuca drimeja, Coronilla emerus, Medicago marina, Alnus cordata, Robinia pseudoacacia, Pinus halepensis* plants, were separately treated with DNAs of all the species applied at the concentration of 500 ppm. Shortly, in Petri plates (9 cm diameter) are placed 10 seeds of each species on a sheet of sterile filter paper. The different DNAs at concentration of 500 ppm were added to the plates whereas only sterile $H_2O$ was added to the control. The germination of the species seeds and the total root length were quantified after 7 days of incubation at 24° C. by observation and measurement of the roots. Each treatment was repeated thrice. The results, reported in FIG. 3 (average of the tests carried out on the above reported different species), shows the inhibition of the germination resulting from the exposure to self DNA and the absence of inhibition in the presence of heterologous DNA.

Example 3

Inhibition of *Arabidopsis thaliana, Lycopersicon esculentum, Lepidium sativum* and *Lens esculentum* Plants by Exposure to Self DNAs A third experiment concerned the evaluation, again by germination and root growth tests, of the toxicity on various plant species by nucleic acid extracted from same species. DNAs of *Arabidopsis thaliana, Lycopersicon esculentum, Lepidium sativum* and *Lens esculentum* were obtained by direct extraction from the respective plants and stored in distilled $H_2O$. Successively 10 previously sterilized seeds of each species are placed in Petri plates (9 cm diameter) on a sheet from sterile filter paper. The seeds of each plant are treated separately with the DNAs of the four species at concentrations of 2, 20 and 200 ppm whereas sterile $H_2O$ was added to the control. The experiments were carried out in growth rooms under controlled conditions and complete sterility. The germination of the four species and the total radical length were quantified after 7 days of incubation at 24° C. by observation and measurement of the roots. Each treatment was repeated thrice. The four species shown an analogous behaviour, with a remarkable inhibiting effect in the presence of self DNA and the absence of effects in the presence of DNAs of the other species. The inhibiting effect proved to be positively correlated to the DNA concentration. For exemplary purpose *Arabidopsis thaliana* in the presence of self and *Lycopersicon esculentum* DNAs, respectively, are reported. Similar inhibition results in *Arabidopsis thaliana*, when seeds of this species are exposed to DNA of the same species obtained by amplification of fragments of the same DNA using PCR techniques, are observed.

Example 4

Figure 5:
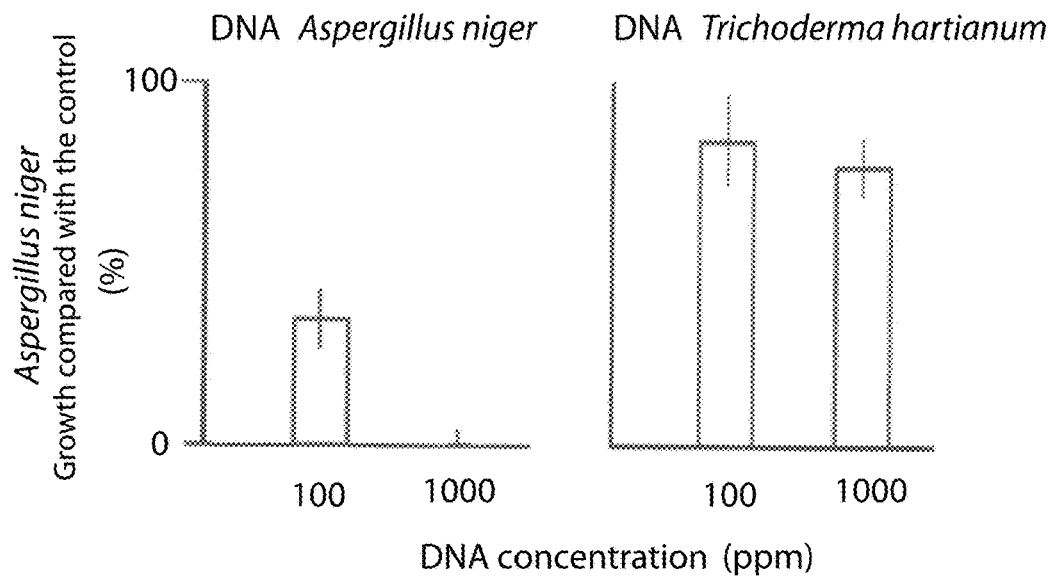
FIG. 5 shows the inhibiting effect on the spore germination and hyphal growth of *Aspergillus niger* when said fungus is exposed to self or other fungus species DNAs (*Trichoderma hartianum*).
Figure 5:
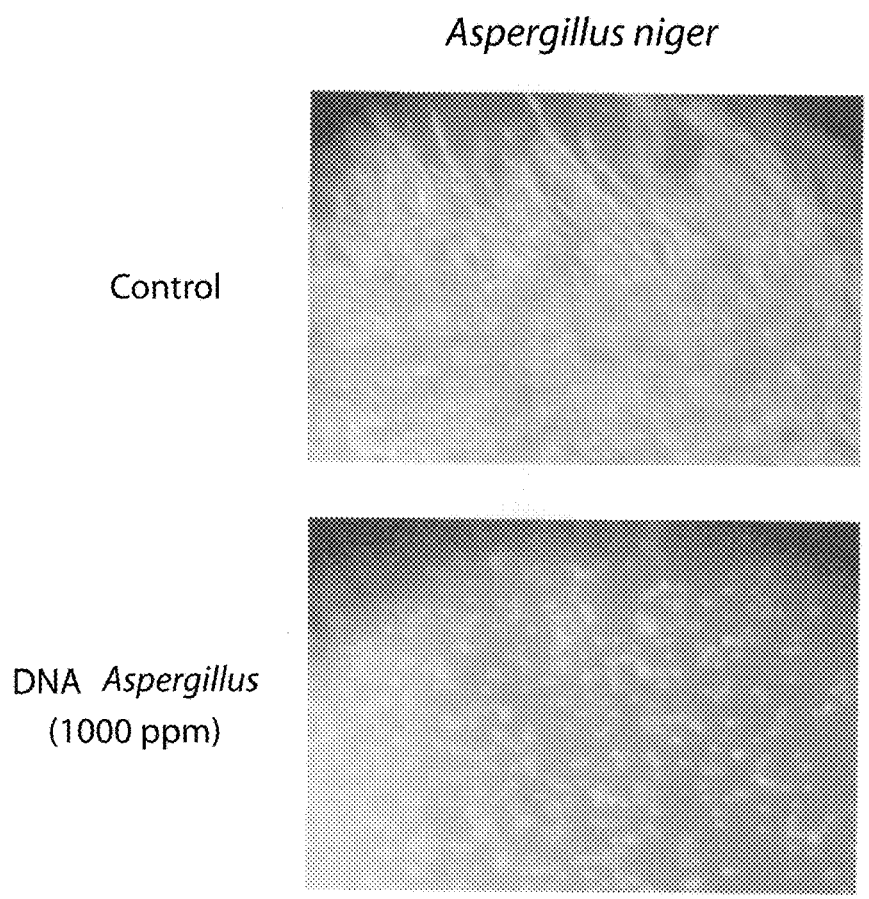

Inhibition of *Aspergillus niger* and *Trichoderma harzianum* Fungi by Exposure to Self DNAs A fourth experiment was carried out on the *Aspergillus niger* fungus in order to estimate the effect of self DNA and DNA isolated from another fungus, i.e. *Trichoderma harzianum*, on the cellular growth. Spores of *Aspergillus niger* are obtained by pure cultures in laboratory on agar treated substrate (PDA, potato dextrose agar). The spores were withdrawn under sterility conditions and diluted at concentration of $1 \times 10^6$ spores/ml. The experiment of germination was carried out in liquid substrate (PDB 10%) in 96 well ELISA plates. The comparative treatment was carried out with DNA of *Trichoderma harzianum*, used as heterologous, whereas the control was not treated. DNAs extracted from both the species were applied at concentrations of 100 and 1000 ppm. Shortly, in each well, with a total volume of 100 µl, said two DNAs separately at different concentrations, together with 10 µl of liquid nutritive substrate (PDB, potato dextrose broth), sterile water and *A. niger* spores were added. The germination of the spores and the length of the germinative tube were quantified by spectrophotometric readings and optical microscope after 20 hours of incubation at 24° C. The results, reported in FIG. 5, show a remarkable inhibiting effect on the germination of the spores and the hyphal growth of *A. niger* only when such fungus was exposed to self DNA.

Example 5

Inhibition of *Sarcophaga carnaria* Insect by Exposure to Self DNA

Figure 7:
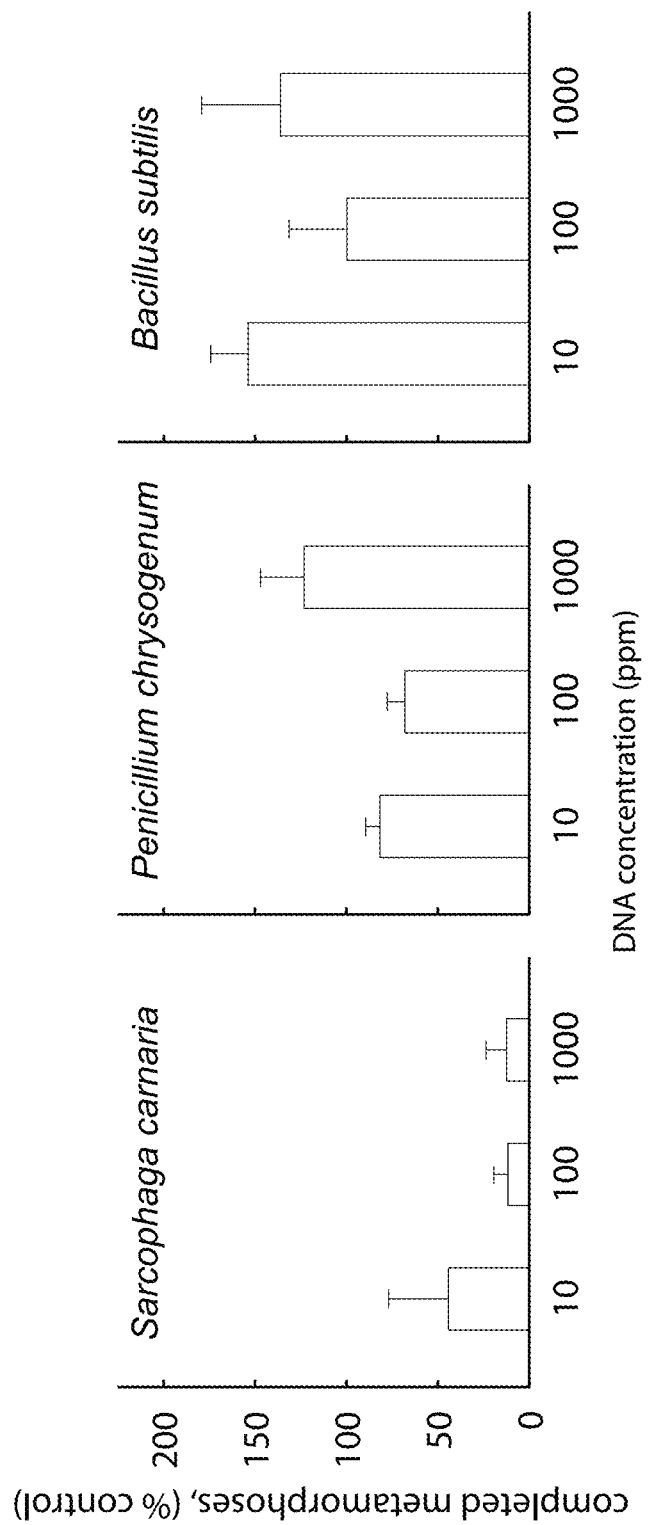
FIG. 7 shows the completed metamorphoses, in percentage compared to not exposed control, in larvae of *Sarcophaga carnaria* dipter exposed for 4 weeks to homologous DNA at three different concentrations, or fungus (*Penicillium chrysogenum*) or bacterium (*Bacillus subtilis*) extracted heterologous DNA.

A fifth experiment was carried out on *Sarcophaga carnaria* insect in order to estimate the effect of self DNA on the life-cycle. Larvae of *Sarcophaga carnaria* dipter were grown in laboratory pure culture at the temperature of 10° C. and fed with minced meat. The experiment of DNA toxicity was carried out in square plastic plates (size 12×12 cm, height 2 cm). The comparative treatments were carried out with DNAs of *Bacillus subtilis* and *Lepidium sativum*, used as heterologous DNA. As control only minced meat without addition of other treatments was used. Dipter and other two species extracted DNAs were added to the minced meat at concentrations of 2, 20 and 200 ppm, under mixer stirring. Shortly, in each plate DNA was added at the various concentrations, stirred with 1 g of minced meat. The plates were incubated at 10° C. in the dark for 21 days. The development, the survival and the time required for the formation of the pupae are monitored every 3 days for the 21 days of incubation. The larvae under control conditions, as well as those treated with heterologous DNA, displayed a regular life-cycle. On the contrary, the exposure to self DNA inhibited the life-cycle causing the death of the larvae proportionally to the treatment concentration. FIGS. 6 and 7 report the above described results.

Example 6

Inhibition of the *Bacillus subtilis* Microorganism by Exposure to Self DNA

Figure 8:
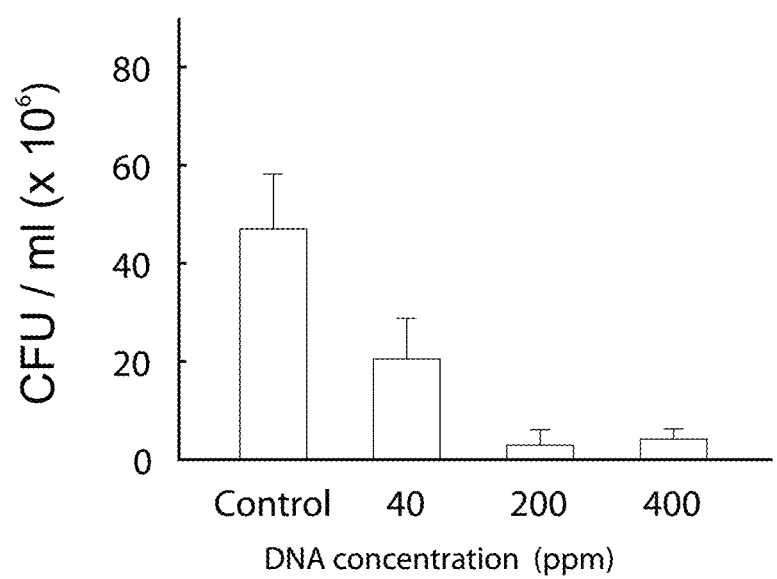
FIG. 8 shows the viable cell counts in *Bacillus subtilis* bacterium in cultures exposed for 24 hours to homologous DNA at three different concentrations and in not exposed control.

In order to demonstrate the possible use of nucleic acid as antibiotics an evaluation of toxicity on *Bacillus subtilis* treated with self DNA at various concentrations was carried out. The experiment was performed using as growth substrate 4 ml of LB (Luria Broth) inoculated with 10 µl of *Bacillus subtilis* preculture. The treatment consisted in the preparation of the cultures in the presence of *Bacillus subtilis* DNA at final concentrations of 4, 40, and 400 ppm. The cultures were incubated under stirring at 35° C. for 24 h with three repeats of treatment. After 24 hours of incubation, from each test tube 0.5 ml was withdrawn and serially diluted in LB medium, from which 100 microliters of agar treated LB medium in Petri plates were plated. The plates were incubated at 28° C. until the appearance of colonies (CFU—colonies forming units). The results reported in FIG. 8 show a remarkable concentration-dependent decrease of CFUs, as response to the treatment.

Example 7

Inhibition of *Trichoderma harzianum* Fungus by Exposure to Self DNA

In order to demonstrate the possible use of nucleic acids as fungicide and action specificity thereof an experiment on the germination of the spores in the *Trichoderma harzianum* fungus was carried out. Spores of *Trichoderma harzianum* were obtained by pure laboratory cultures on agar treated substrate (PDA, potato dextrose agar). The spores were withdrawn under sterility conditions and diluted at concentration of $1\times10^6$ spores/ml. The experiment of germination was carried out in liquid substrate (PDB 10%) in 96 well ELISA plates. The treatment was carried out with homologous or heterologous DNA, that is extracted from the same species of *Trichoderma*, or from a different species of fungus (*Aspergillus niger*), from an insect (*Sarcophaga carnaria*) or from a bacterium (*Bacillus subtilis*). The DNA extracted from the different species was applied at concentrations of 8, 80 and 800 ppm. Shortly, in each well, with a total volume of 100 µl, DNA separately at different concentrations, together with 10 µl of liquid nutritive substrate (PDB, potato dextrose broth), sterile water and *Trichoderma* spores were added. The germination of the spores and the length of the germinative tube were quantified by spectrophotometric readings and optical microscope after 20 hours of incubation at 24° C.

Figure 9:
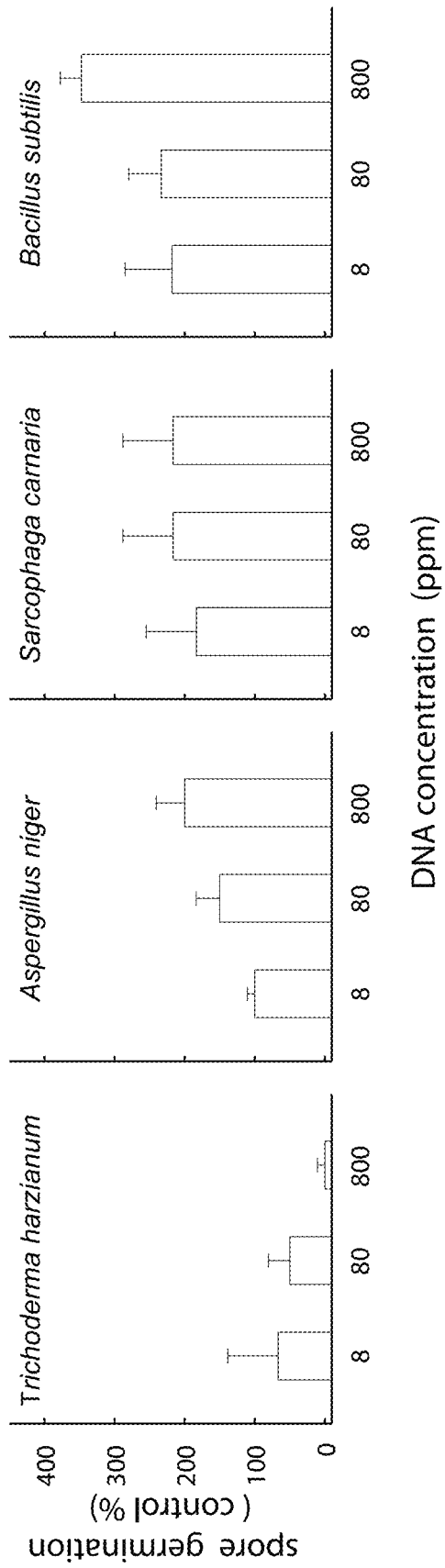
FIG. 9 shows the germination of the spores in the *Trichoderma harzianum* fungus, in percentage compared to not exposed control, in cultures exposed to homologous DNA at three different concentrations, or to heterologous DNA extracted from other fungus (*Aspergillus niger*), insect (*Sarcophaga carnaria*) or bacterium (*Bacillus subtilis*).

FIG. 9 indicates the results of the experiment showing a remarkable concentration-dependent inhibiting effect, on the germination of the *Trichoderma* spores only by DNA of the same fungus species. On the contrary, the treatment with various species DNAs display stimulating effects on the germination (percentage values compared to not exposed control higher than 100%).

Example 8

Inhibition of the *Scenedesmus obliquus* Microalga by Exposure to Self DNA

Figure 10:
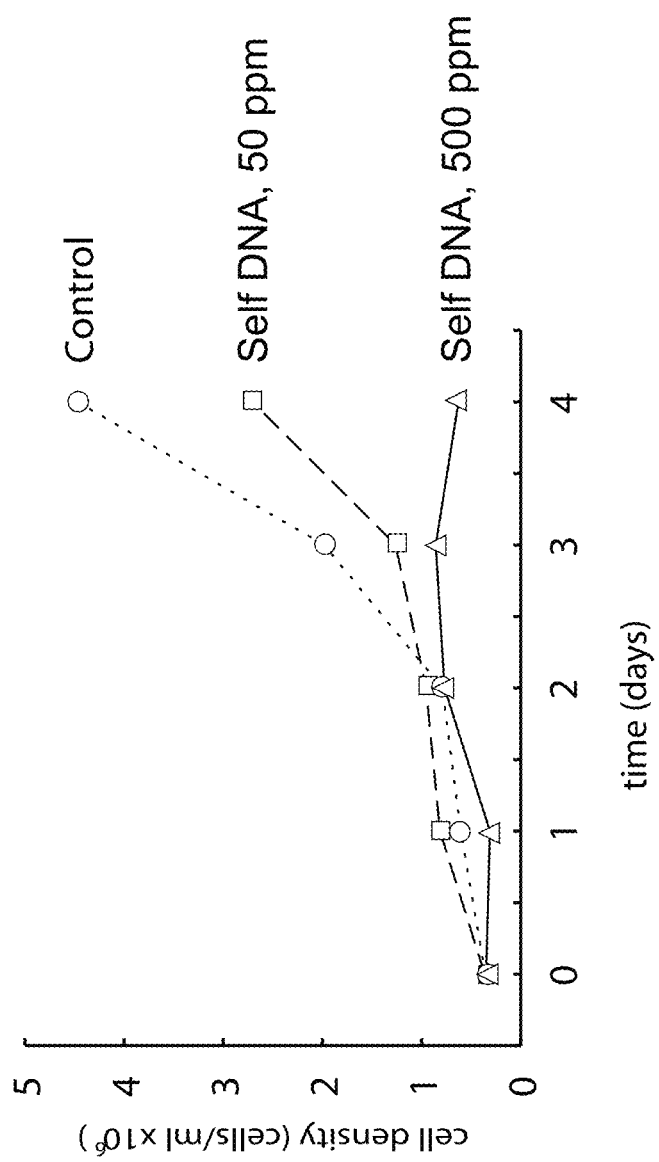
FIG. 10 shows growth dynamics of *Scenedesmus obliquus* microalga in two cultures exposed to homologous DNA at different concentration, and not exposed control.

In order to demonstrate the possible DNA use as algicide product a growth test of *Scenedesmus obliquus* green alga under optimal control conditions and self DNA presence was carried out in the culture substrate (CHU #10). The treatments were carried out at two different concentrations (50 and 500 ppm) with two repeats. FIG. 10 shows the growth dynamics of the alga and shows a remarkable concentration-dependent inhibiting effect of the homologous DNA compared to not exposed control.

Example 9

Inhibition of the *Physarium polycephalum* Protozoan by Exposure to Self DNA In order to demonstrate the possible DNA use as antiprotozoic product an experiment was carried out on *Physarium polycephalum* protozoan. As experimental material the culture kit produced from "Carolina Biological Supply" was used. The cultures started on Petri plates with water-agar in order to favour the movement of the organism. As nutriment oat flakes were used. A first bulk culture was carried out on 20 plates and protozoic biomass produced after 15 days was collected and used for DNA extraction using Quiagen kit. The successive experiment consisted of the preparation of three Petri plates filled up with water agar to which two small portions of oats flakes were added, one for control wetted with 5 ml of distilled water and the other with addition of 5 ml of water with DNA of the protozoan at concentration of 200 ppm. The experiment was repeated other two times, with the variation that the added DNA was from bacterium (*Bacillus subtilis*) and insect (*Sarcophaga carnaria*). The results of the experiments shown the absence of growth of *Physarium polycephalum* on the substrate treated with DNA of the same protozoan whereas the organism did not shown growth differences under control conditions or heterologous DNA presence.

Example 10

Study of Production Process of Yeasts, Bacteria and Algae in Bioreactors and Photobioreactors Considering the above reported demonstrations about the inhibiting effect on different species when exposed to self DNAs, check analyses were carried out on the extracellular DNA presence in the growth substrate in bioreactors and photobioreactors with cellular cultures at high density when conditions of growth slowing down, even if under optimal nutritive substrate presence, occur. The study involved the sampling of liquid supernatant of different cultures in bioreactors in exponential growth, slowing down and steady-state stages. The analysis concerned cultures of *Saccharomyces cerevisiae* yeast, *Bacillus subtilis* bacterium and *Phaeodactylum tricornutum* and *Scenedesmus obliquus* microalgae. Samples of the cellular culture supernatants obtained by two cycles of centrifugation at 3000 rpm for 15 minutes were analyzed in order to separate possible cell residues and then subjected to gel electrophoresis after treatment with Syber-Safe and fluorescence evaluation. FIG. 11 shows the results of some of these analyses from which it is apparent the accumulation of extracellular DNA in the liquid substrate of the bioreactors. This accumulation is clearly associated to the slowing down of the growth of the different cellular cultures and to the attainment of the steady-state stage (FIGS. 11A and 11B). FIG. 11C shows clearly as the removal of the extracellular DNA from culture medium by chemical-physical procedures and the following introduction of regenerated substrate into the reactor results in the elimination of the inhibiting effect and a consequent restoring of the cellular culture growth.

The invention claimed is:
1. A method for growing an organism in a culture system comprising a culture medium, the method comprising
    removing from the culture medium extracellular DNA of the organism to provide a regenerated medium; and
    culturing the organism in the regenerated medium,
wherein the organism is a microorganism or a plant.
2. The method according to claim 1, wherein the culture medium is within a bioreactor, a photobioreactor or a system for hydroponic culture.
3. The method according to claim 2, wherein the removing is performed by an external removal unit external to the bioreactor, photobioreactor or system for hydroponic culture.
4. The method according to claim 3, wherein the external removal unit comprises an external container and a system for generating of electric, or magnetic, or electromagnetic fields and displacing DNA from the bioreactor, the photobioreactor or a system for hydroponic culture.

5. The method according to claim 2, wherein the removing is performed by an internal removal unit integrated into the bioreactor, photobioreactor or system for hydroponic culture.

6. The method according to claim 5, wherein the internal removal unit comprises a system for generating electric, or magnetic, or electromagnetic fields and displacing DNA from the culture medium, the system integrated within the bioreactor, photobioreactor or system for hydroponic culture.

7. The method according to claim 1, wherein the removing is performed by applying to the culture medium an electric, magnetic, or electromagnetic field to remove the extracellular DNA from the culture medium.

8. The method according to claim 1, wherein the removing is performed by centrifugating the culture medium, to remove the extracellular DNA from the culture medium.

9. The method according to claim 1, wherein the removing is performed by filtrating the culture medium to remove the extracellular DNA from the culture medium.

10. The method according to claim 1, wherein the removing is performed by treating the culture medium with degrading enzymes, to remove the extracellular DNA from the culture medium.

11. The method according to claim 1, wherein the removing is performed by heat treating the culture medium to remove the extracellular DNA from the culture medium.

12. The method according to claim 1, wherein the removing is performed by performing acidifying treatments of the culture medium to remove the extracellular DNA from the culture medium.

13. The method according to claim 1, further comprising collecting the extracellular DNA removed from the culture medium.

14. The method according to claim 1, wherein the DNA comprises fragments of 80 to 800 bp.

* * * * *